(12) United States Patent
Takemoto et al.

(10) Patent No.: US 7,625,689 B2
(45) Date of Patent: Dec. 1, 2009

(54) CHEMICALLY AMPLIFIED POSITIVE RESIST COMPOSITION

(75) Inventors: Ichiki Takemoto, Kawanishi (JP); Satoshi Yamaguchi, Toyonaka (JP); Hiromu Sakamoto, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 303 days.

(21) Appl. No.: 11/303,925

(22) Filed: Dec. 19, 2005

(65) Prior Publication Data

US 2006/0160017 A1    Jul. 20, 2006

(30) Foreign Application Priority Data

Dec. 22, 2004   (JP)   ............... 2004-370728

(51) Int. Cl.
*G03C 1/00*   (2006.01)
*C07C 69/74*  (2006.01)

(52) U.S. Cl. ....................... 430/270.1; 560/1
(58) Field of Classification Search ............. 430/270.1; 560/1
See application file for complete search history.

(56) References Cited

U.S. PATENT DOCUMENTS

| | | | | | |
|---|---|---|---|---|---|
| 4,068,082 | A | * | 1/1978 | Stoffey et al. | 560/90 |
| 5,672,779 | A | * | 9/1997 | Iwasaki et al. | 568/838 |
| 2005/0260525 | A1 | * | 11/2005 | Takemoto et al. | 430/270.1 |
| 2005/0266351 | A1 | * | 12/2005 | Takemoto et al. | 430/311 |
| 2006/0014913 | A1 | * | 1/2006 | Lee et al. | 526/266 |

FOREIGN PATENT DOCUMENTS

| | | | |
|---|---|---|---|
| JP | 2000-10285 A | | 1/2000 |
| JP | 2000010285 A | * | 1/2000 |
| JP | 2000-302839 A | | 10/2000 |
| JP | 2000302839 A | * | 10/2000 |
| JP | 2003241366 A | * | 8/2003 |
| JP | 2005-75767 A | | 3/2005 |

OTHER PUBLICATIONS

Sato et al. JP 2000-010285 A, English translation (machine translation).*
Sato et al., JP 2000-302839 A, English translation (machine translation).*

* cited by examiner

*Primary Examiner*—Cynthia H Kelly
*Assistant Examiner*—Connie P Johnson
(74) *Attorney, Agent, or Firm*—Birch, Stewart, Kolasch & Birch, LLP

(57) ABSTRACT

The present invention provides a chemically amplified positive resist composition comprising
(i) a polymer which is insoluble or poorly soluble in an alkali aqueous solution but becomes soluble in an alkali aqueous solution by the action of an acid,
(ii) an acid generator, and
(iii) a compound of the formula (I).

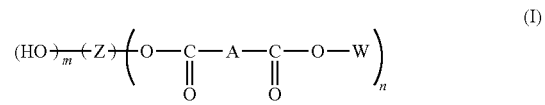

The present invention also provides an ester derivative useful as a component of the chemically amplified positive resist composition, and process for producing the ester derivative.

7 Claims, No Drawings

CHEMICALLY AMPLIFIED POSITIVE RESIST COMPOSITION

This nonprovisional application claims priority under 35 U.S.C. § 119(a) on Patent Application No. 2004-370728 filed in JAPAN on Dec. 22, 2004, the entire contents of which are hereby incorporated by reference.

FIELD OF THE INVENTION

The present invention relates to a chemically amplified positive resist composition for use in micro fabrication of semiconductor, a supramolecule useful for a component of the resist composition, and a process for producing thereof.

BACKGROUND OF THE INVENTION

Semiconductor microfabrication employs a lithography process using a resist composition. In lithography, theoretically, the shorter the exposure wavelength becomes, the higher the resolution can be made, as expressed by Rayleigh's diffraction limit formula. The wavelength of an exposure light source for lithography used in the manufacture of semiconductor devices has been shortened year by year as g line having a wavelength of 436 nm, i line having a wavelength of 365 nm, KrF excimer laser having a wavelength of 248 nm and ArF excimer laser having a wavelength of 193 nm. Further, as the exposure light source of the subsequent generation, soft X ray (EUV) having a wavelength of 13 nm or shorter has been proposed as the exposure light source.

As line width has become narrower in lithography process using light sources having shorter wavelength, such as excimer laser and the like, especially line edge roughness (roughness of pattern surfaces or wave of pattern, abbreviated by LER), as well as resolution, sensitivity and pattern shape, has become important subject (e.g. Proc. of SPIE Vol. 5038 (2003), 689-698).

With further advance of microfabrication technology, it is required for new photoresist compositions to show more advantageous abilities than conventional photoresists. Specifically, photoresist compositions giving better resolution, sensitivity, pattern profiles to resist pattern obtained therefrom, especially giving better line edge roughness are required.

SUMMARY OF THE INVENTION

An object of the present invention is to provide a chemically amplified resist composition suitable for ArF excimer laser lithography, showing excellent various resist abilities such as resolution, sensitivity, pattern shape and the like, and giving particularly excellent line edge roughness.

Another object of the present invention is to provide a supramolecule useful for a component of a photoresist composition.

Still another object of the present invention is to provide a process for producing the supramolecule.

These and other objects of the present invention will be apparent from the following description.

The present invention relates to the followings:
<1> A chemically amplified positive resist composition comprising
(i) a polymer which is insoluble or poorly soluble in an alkali aqueous solution but becomes soluble in an alkali aqueous solution by the action of an acid,
(ii) an acid generator, and
(iii) a compound of the formula (I)

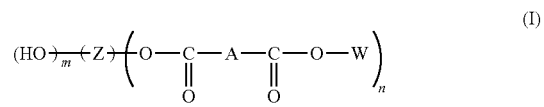

wherein Z represents hydrocarbon group having 2 to 14 carbon atom, and at least one of —$CH_2$— except the one bonding to other group adjacent to Z may be substituted by —O—; A represents divalent alicyclic hydrocarbon group having 3 to 14 carbon atoms; W represents hydrogen atom, alkyl group having 1 to 12 carbon atoms, alkoxyalkyl group having 2 to 12, or a group of the formula (II)

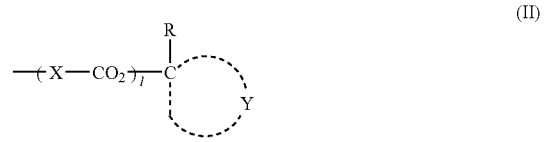

wherein X represents divalent connecting group, R represents hydrogen atom, alkyl group having 1 to 6 carbon atoms or cycloalkyl group having 3 to 6 carbon atoms, Y represents atoms necessary to form an alicyclic hydrocarbon group together with the adjacent carbon atom and contains 4 to 12 carbon atoms, and at least one of —$CH_2$— in the alicyclic hydrocarbon group may be substituted by —CO— or —O—, and at least one of hydrogen atoms in the alicyclic hydrocarbon group may be substituted by alkyl group having 1 to 4 carbon atoms, alkoxy group having 1 to 4 carbon atoms, trifluoromethyl group, hydroxyl group or cyano group, and l represents 0 or 1, and
each of m and n shows an integer satisfying the following inequalities.
$0 \leq m \leq 13$, $1 \leq n \leq 14$, $2 \leq m+n \leq 14$, and
when n is 2 or more, each of A is the same or the different, and also each of W is the same or the different.

<2> The composition according to <1>, wherein Z is saturated acyclic hydrocarbon group having 2 to 14 carbon atoms or saturated alicyclic hydrocarbon group having 3 to 14 carbon atoms, wherein at least one of —$CH_2$— group except the one bonding to other group adjacent to Z may be substituted by —O—; A is divalent saturated alicyclic hydrocarbon group; and X is divalent saturated acyclic hydrocarbon group or divalent saturated alicyclic hydrocarbon group, wherein at least one of —$CH_2$— in the hydrocarbon group except the one bonding to other group adjacent to X may be substituted by —O—, —COO— or —O—CO—.

<3> The composition according to <1>, wherein the compound of the formula (I) is a compound of the formula (III)

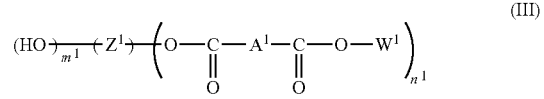

wherein $Z^1$ represents a hydrocarbon group having 3 to 6 carbon atoms, and at least one of —$CH_2$— except the one bonding to other group adjacent to $Z^1$ may be substituted by —O—; $A^1$ represents divalent alicyclic hydrocarbon group having 5 to 10 carbon atoms; $W^1$ represents hydrogen atom, alkyl group having 1 to 10 carbon atoms, alkoxyalkyl group having 2 to 6, or a group of the formula (IV)

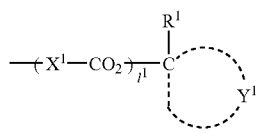

(IV)

wherein $X^1$ represents methylene group, ethylene group, trimethylene group, tetramethylene group, or 6-hydroxy-2-norbornanecarboxylic acid γ-lactone-3,5-diyl group, $R^1$ represents hydrogen atom, alkyl group having 1 to 4 carbon atoms or cycloalkyl group having 3 to 6 carbon atoms, $Y^1$ represents atoms necessary to form an alicyclic hydrocarbon group together with the adjacent carbon atom and contains 4 to 10 carbon atoms, and at least one of —$CH_2$— in the alicyclic hydrocarbon group may be substituted by —CO— or —O—, and at least one of hydrogen atoms in the alicyclic hydrocarbon group may be substituted by alkyl group having 1 to 6 carbon atoms, alkoxy group having 1 to 6 carbon atoms, perfluoroalkyl group having 1 to 4 carbon atoms, hydroxyl group or cyano group, and $1^1$ represents 0 or 1, and $m^1$ and $n^1$ shows an integer satisfying all of the following inequalities.

$0 \leq m^1 < 13$, $1 \leq n^1 \leq 14$, $2 \leq m^1+n^1 \leq 14$, and when $n^1$ is 2 or more, each of $A^1$ is the same or the different, and each of $W^1$ is the same or the different.

<4> The composition according to <3>, wherein $Z^1$ is saturated acyclic hydrocarbon group having 3 to 6 carbon atoms or saturated alicyclic hydrocarbon group having 3 to 6 carbon atoms, wherein at least one of —$CH_2$— group except the one bonding to other group adjacent to $Z^1$ may be substituted by —O—; and $A^1$ is divalent saturated alicyclic hydrocarbon group having 5 to 10 carbon atoms.

<5> The composition according to <1>, wherein the compound of the formula (I) is a compound of the formula (V)

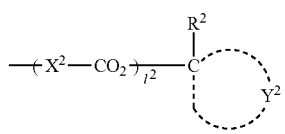

(V)

wherein $Z^2$ represents a group selected by the following formulae

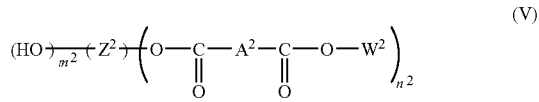

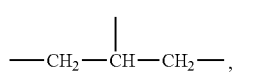 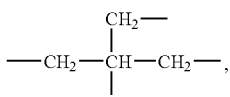

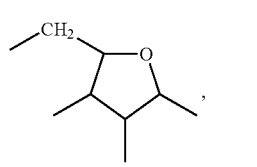, 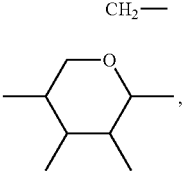

-continued

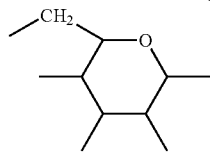

wherein a straight line with an open end shows a bond which is extended from an adjacent carbon atom and which does not specifies a group to be bonded, $A^2$ represents cyclopentylene group, cyclohexylene group, norbornylene group or adamantylene group; $W^2$ represents hydrogen atom, methyl group, ethyl group, isopropyl group, butyl group, methoxymethyl group, ethoxymethyl group, propoxymethyl group, methoxyethyl group, ethoxyethyl group, or a group of the formula (VI)

(VI)

$-(X^2-CO_2)_{l^2}-C(R^2)(Y^2)$ wherein $X^2$ represents methylene group or ethylene group, $R^2$ represents hydrogen atom, methyl group, ethyl group, isopropyl group, butyl group, cyclopentyl group or cyclohexyl group, $Y^2$ represents atoms necessary to form cyclopentyl group, cyclohexyl group, norbornyl group or adamantyl group together with the adjacent carbon atom, and at least one of —$CH_2$— in the cyclopentyl group, cyclohexyl group, norbornyl group or adamantyl group may be substituted by —CO— or —O—, and at least one of hydrogen atoms in the cyclopentyl group, cyclohexyl group, norbornyl group or adamantyl group may be substituted by methyl group, ethyl group, isopropyl group, butyl group, methoxy group, ethoxy group, propoxy group trifluoromethyl group, hydroxyl group or cyano group, and $1^2$ represents 0 or 1, and $m^2$ and $n^2$ shows an integer satisfying all of the following inequalities.

$0 \leq m^2 \leq 4$, $1 \leq n^2 \leq 5$, $2 \leq m^2+n^2 \leq 5$ and when $n^2$ is 2 or more, each of $A^2$ is the same or the different, and also each of $W^2$ is the same or the different.

<6> An ester derivative of the formula (VII)

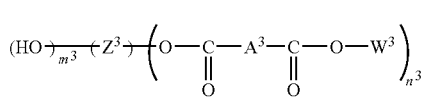

(VII)

wherein $Z^3$ represents hydrocarbon group having 2 to 14 carbon atom, and at least one of —$CH_2$— except the one bonding to other group adjacent to $Z^3$ may be substituted by —O—; $A^3$ represents divalent alicyclic hydrocarbon group having 3 to 14 carbon atoms; $W^3$ represents hydrogen atom, alkyl group having 1 to 12 carbon atoms or a group of the formula (VIII)

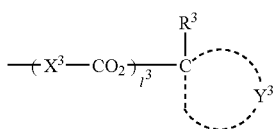

(VIII)

wherein $X^3$ represents divalent connecting group, $R^3$ represents hydrogen atom, alkyl group having 1 to 6 carbon atoms or cycloalkyl group having 3 to 6 carbon atoms, $Y^3$ represents atoms necessary to form an alicyclic hydrocarbon group together with the adjacent carbon atom and contains 3 to 12 carbon atoms, and at least one of —$CH_2$— in the alicyclic hydrocarbon group may be substituted by —CO— or —O—, and at least one of hydrogen atoms in the alicyclic hydrocarbon group may be substituted by alkyl group having 1 to 6 carbon atoms, alkoxy group having 1 to 6 carbon atoms, perfluoroalkyl group having 1 to 4 carbon atoms, hydroxyl group or cyano group, and $l^3$ represents 0 or 1, and $m^3$ and $n^3$ show an integer satisfying all of the following inequalities, $0 \leq m^3 \leq 13$, $1 \leq n^3 \leq 14$, $2 \leq m^3+n^3 \leq 14$, and when $n^3$ is 2 or more, each of $A^3$ is the same or the different, and also each of $W^3$ is the same or the different.

<7> The ester derivative according to <6>, wherein $Z^3$ is saturated acyclic hydrocarbon group having 2 to 14 carbon atoms or saturated alicyclic hydrocarbon group having 3 to 14 carbon atoms, wherein at least one of —$CH_2$— group except the one bonding to other group adjacent to $Z^3$ may be substituted by —O—; $A^3$ is divalent saturated alicyclic hydrocarbon group; and $X^3$ is divalent saturated acyclic hydrocarbon group or divalent saturated alicyclic hydrocarbon group, wherein at least one of —$CH_2$— in the hydrocarbon group except the one bonding to other group adjacent to $X^3$ may be substituted by —O—, —COO— or —O—CO—.

<8> A process for producing a compound of the formula (VII')

(VII')

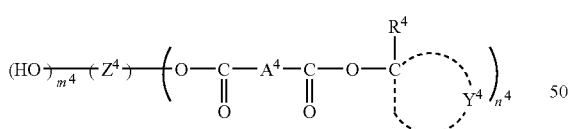

wherein $Z^4$ represents hydrocarbon group having 2 to 14 carbon atom, and at least one of —$CH_2$— except the one bonding to other group adjacent to $Z^4$ may be substituted by —O—; $A^4$ represents divalent alicyclic hydrocarbon group having 3 to 14 carbon atoms; $R^4$ represents hydrogen atom, alkyl group having 1 to 6 carbon atoms or cycloalkyl group having 3 to 6 carbon atoms, $Y^4$ represents atoms necessary to form an alicyclic hydrocarbon group together with the adjacent carbon atom and contains 3 to 12 carbon atoms, and at least one of —$CH_2$— in the alicyclic hydrocarbon group may be substituted by —CO— or —O—, and at least one of hydrogen atoms in the alicyclic hydrocarbon group may be substituted by alkyl group having 1 to 6 carbon atoms, alkoxy group having 1 to 6 carbon atoms, perfluoroalkyl group having 1 to 4 carbon atoms, hydroxyl group or cyano group, and each of $m^4$ and $n^4$ shows an integer satisfying the following inequalities.

$0 \leq m^4 \leq 13$, $1 \leq n^4 \leq 14$, $2 \leq m^4+n^4 \leq 14$, and when $n^4$ is 2 or more, each of $A^4$ is the same or the different, each of $R^4$ is the same or the different, and each of alicyclic hydrocarbon group formed by $Y^4$ and the carbon atom adjacent to $Y^4$ is the same or different, which comprises a step comprising reacting a compound of the formula (IX)

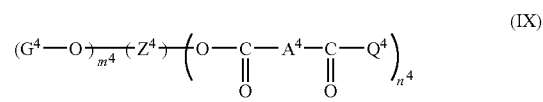

(IX)

wherein Q represents chlorine atom, bromine atom, iodine atom or imidazolyl group, $G^4$ represents a group protecting hydroxyl group, and $Z^4$, $A^4$, $m^4$ and $n^4$ have the same meanings as defined above, with an alcohol derivative of the formula (X)

(X)

wherein $R^4$ and $Y^4$ have the same meanings as defined above, in the presence of deacidifying agent, and a step subjecting the reaction product obtained by the step above to deprotection.

<9> The process according to <8>, wherein $Z^4$ is saturated acyclic hydrocarbon group having 2 to 14 carbon atoms or saturated alicyclic hydrocarbon group having 3 to 14 carbon atoms, wherein at least one of —$CH_2$— group except the one bonding to other group adjacent to $Z^4$ may be substituted by —O—; and $G^4$ is trialkylsilyl group.

<10> A process for producing a compound of the formula (VII")

(VII")

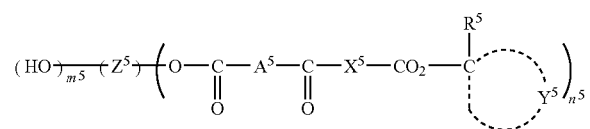

wherein $Z^5$ represents hydrocarbon group having 2 to 14 carbon atom, and at least one of —$CH_2$— except the one bonding to other group adjacent to $Z^5$ may be substituted by —O—; $A^5$ represents divalent alicyclic hydrocarbon group having 3 to 14 carbon atoms; $X^5$ represents divalent connecting group; $R^5$ represents hydrogen atom, alkyl group having 1 to 6 carbon atoms or cycloalkyl group having 3 to 6 carbon atoms, $Y^5$ represents atoms necessary to form an alicyclic hydrocarbon group together with the adjacent carbon atom and contains 3 to 12 carbon atoms, and at least one of —CH$_2$— in the alicyclic hydrocarbon group may be substituted by —CO— or —O—, and at least one of hydrogen atoms in the alicyclic hydrocarbon group may be substituted by alkyl group having 1 to 6 carbon atoms, alkoxy group having 1 to 6 carbon atoms, perfluoroalkyl group having 1 to 4 carbon atoms, hydroxyl group or cyano group, and each of m$^5$ and n$^5$ shows an integer satisfying the following inequalities.

$0 \leq m^5 \leq 13$, $1 \leq n^5 \leq 14$, $2 \leq m^5+n^5 \leq 14$, and when n$^5$ is 2 or more, each of A$^5$ is the same or the different, each of R$^5$ is the same or the different, each of X$^5$ is the same or the different, and each of alicyclic hydrocarbon group formed by Y$^5$ and the carbon atom adjacent to Y$^5$ is the same or different, which comprises reacting a compound of the formula (XI)

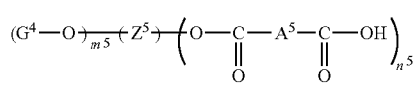

wherein G$^5$ represents hydrogen atom or a group protecting hydroxyl group, and Z$^5$, A$^5$, m$^5$ and n$^5$ have the same meanings as defined above, with a compound of the formula (XII)

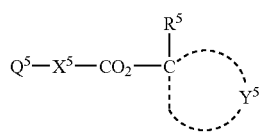

wherein Q$^5$ represents chlorine atom, bromine atom or iodine atom, X$^5$, R$^5$ and Y$^5$ have the same meanings as defined above, in the presence of deacidifying agent, and further comprises subjecting the reaction product obtained by the reaction of the compounds (XI) and (XII) above to deprotection when G$^5$ is the group protecting hydroxyl group.

<11> The composition according to <10>, wherein Z$^5$ is saturated acyclic hydrocarbon group having 2 to 14 carbon atoms or saturated alicyclic hydrocarbon group having 3 to 14 carbon atoms, wherein at least one of —CH$_2$— group except the one bonding to other group adjacent to Z$^5$ may be substituted by —O—; A$^5$ is divalent saturated alicyclic hydrocarbon group; and X$^5$ is divalent saturated acyclic hydrocarbon group or divalent saturated alicyclic hydrocarbon group, wherein at least one of —CH$_2$— in the hydrocarbon group except the one bonding to other group adjacent to X$^5$ may be substituted by —O—, —COO— or —O—CO—.

Hereinafter, "compound of the formula (I)", "compound of the formula (III)", "compound of the formula (V)", "ester derivative of the formula (VII)", "ester derivative of the formula (VII')", "ester derivative of the formula (VII")", "compound of the formula (IX)", "alcohol derivative of the formula (X)", "compound of the formula (XI)" and "compound of the formula (XII)" may be referred to as "Supracompound (I)", "Supracompound (III)", "Supracompound (V)", "Ester Derivative (VII)", "Ester Derivative (VII')", "Ester Derivative (VII")", "Compound (IX)", "Alcohol Derivative (X)", "Compound (XI)" and "Compound (XII)", respectively.

DESCRIPTION OF PREFERRED EMBODIMENTS

The present composition useful for a chemically amplified photoresist comprises
(i) a polymer which is insoluble or poorly soluble in an alkali aqueous solution but becomes soluble in an alkali aqueous solution by the action of an acid, (ii) an acid generator, and (iii) Supracompound (I).

In Supracompound (I), Z represents hydrocarbon group having 2 to 14 carbon atom, preferably saturated acyclic hydrocarbon group having 2 to 14 carbon atoms and saturated alicyclic hydrocarbon group having 3 to 14 carbon atoms, more preferably saturated acyclic hydrocarbon group having 3 to 6 carbon atoms and saturated alicyclic hydrocarbon group having 3 to 6 carbon atoms. And at least one of —CH$_2$— except the one bonding to other group adjacent to Z may be substituted by —O—. A represents divalent alicyclic hydrocarbon group having 3 to 14 carbon atoms, preferably 3 to 10 carbon atoms, more preferably 3 to 8 carbon atoms. W represents hydrogen atom, alkyl group having 1 to 12 carbon atoms, alkoxyalkyl group having 2 to 12, or a group of the formula (II), preferably hydrogen atom, alkyl group having 1 to 10 carbon atoms, alkoxyalkyl group having 2 to 6, or a group of the formula (IV), more preferably hydrogen atom, ethyl group, isopropyl group butyl group, methoxymethyl group, ethoxymethyl group, propoxymethyl group, methoxyethyl group, ethoxyethyl group or a group of the formula (VI).

X in the group of the formula (II) represents divalent connecting group; preferably divalent saturated acyclic hydrocarbon group or divalent saturated alicyclic hydrocarbon group, wherein at least one of —CH$_2$— in the saturated acyclic or alicyclic hydrocarbon group except the one bonding to other group adjacent to X may be substituted by —O—, —COO— or —OCO—; more preferably methylene group, ethylene group, trimethylene group or tetramethylene group; more preferably methylene group or ethylene group. Y in the group of the formula (II) represents atoms necessary to form an alicyclic hydrocarbon group together with the adjacent carbon atom and contains 4 to 12, preferably 4 to 10 carbon atoms; more preferably atoms necessary to form cyclopentyl group, cyclohexyl group, norbornyl group or adamantyl group together with the adjacent carbon atom. R represents hydrogen atom, alkyl group having 1 to 6 carbon atoms or cycloalkyl group having 3 to 6 carbon atoms, preferably hydrogen atom, alkyl group having 1 to 4 carbon atoms or cycloalkyl group having 3 to 6 carbon atoms, more preferably hydrogen atom, methyl group, ethyl group, isopropyl group, butyl group, cyclopentyl group or cyclohexyl group.

Each of m and n in the formula (I) shows an integer satisfying the inequalities of $0 \leq m \leq 13$, $1 \leq n \leq 14$ and $2 \leq m+n \leq 14$, and preferably of $0 \leq m \leq 4$, $1 \leq n \leq 5$ and $2 \leq m+n \leq 5$. l represents 0 or 1.

In Ester Derivative (VII), Ester Derivative (VII') and Ester Derivative (VII"), each of Z$^3$, Z$^4$ and Z$^5$ represents hydrocarbon group having 2 to 14 carbon atom, preferably saturated acyclic hydrocarbon group having 2 to 14 carbon atoms and saturated alicyclic hydrocarbon group having 3 to 14 carbon atoms, more preferably saturated acyclic hydrocarbon group having 3 to 6 carbon atoms and saturated alicyclic hydrocarbon group having 3 to 6 carbon atoms. And at least one of —CH$_2$— except the one bonding to other group adjacent to Z$^3$, Z$^4$ or Z$^5$ may be substituted by —O—. Each of A$^3$, A$^4$ and $A^5$ represents divalent alicyclic hydrocarbon group having 3 to 14 carbon atoms, preferably 3 to 10 carbon atoms, more preferably 3 to 8 carbon atoms. $W^3$ represents hydrogen atom, alkyl group having 1 to 12 carbon atoms, alkoxyalkyl group having 2 to 12, or a group of the formula (VIII), preferably hydrogen atom, alkyl group having 1 to 10 carbon atoms, alkoxyalkyl group having 2 to 6, or a group of the formula (IV), more preferably hydrogen atom, ethyl group, isopropyl group butyl group, methoxymethyl group, ethoxymethyl group, propoxymethyl group, methoxyethyl group, ethoxyethyl group or a group of the formula (VI).

In the group of the formula (VIII) and Ester Derivative (VII″), each of $X^3$ and $X^5$ represents divalent connecting group; preferably divalent saturated acyclic hydrocarbon group or divalent saturated alicyclic hydrocarbon group, wherein at least one of —$CH_2$— in the saturated acyclic or alicyclic hydrocarbon group except the one bonding to other group adjacent to $X^3$ or $X^5$ may be substituted by —O—, —COO— or —OCO—; more preferably methylene group, ethylene group, trimethylene group or tetramethylene group; more preferably methylene group or ethylene group. In the group of the formula (VIII), Ester Derivative (VII′) and Ester Derivative (VII″), each of $Y^3$, $Y^4$ and $Y^5$ represents atoms necessary to form an alicyclic hydrocarbon group together with the adjacent carbon atom and contains 4 to 12, preferably 4 to 10 carbon atoms; more preferably atoms necessary to form cyclopentyl group, cyclohexyl group, norbornyl group or adamantyl group together with the adjacent carbon atom. Each of $R^3$, $R^4$ and $R^5$ represents hydrogen atom, alkyl group having 1 to 6 carbon atoms or cycloalkyl group having 3 to 6 carbon atoms, preferably hydrogen atom, alkyl group having 1 to 4 carbon atoms or cycloalkyl group having 3 to 6 carbon atoms, more preferably hydrogen atom, methyl group, ethyl group, isopropyl group, butyl group, cyclopentyl group or cyclohexyl group.

Each of $m^3$ and $n^3$ in the formula (VII) shows an integer satisfying the inequalities of $0 \leq m^3 \leq 13$, $1 \leq n^3 \leq 14$ and $2 \leq m^3+n^3 \leq 14$, and preferably of $0 \leq m^3 \leq 4$, $1 \leq n^3 \leq 5$ and $2 \leq m^3+n^3 \leq 5$. $1^3$ represents 0 or 1.

Each of $m^4$ and $n^4$ in the formula (VII′) shows an integer satisfying the inequalities of $0 \leq m^4 \leq 13$, $1 \leq n^4 \leq 14$ and $2 \leq m^4+n^4 \leq 14$, and preferably of $0 \leq m^4 \leq 4$, $1 \leq n^4 \leq 5$ and $2 \leq m^4+n^4 \leq 5$.

Each of $m^5$ and $n^5$ in the formula (VII″) shows an integer satisfying the inequalities of $0 \leq m^5 \leq 13$, $1 \leq n^5 \leq 14$ and $2 \leq m^5+n^5 \leq 14$, and preferably of $0 \leq m^5 \leq 4$, $1 \leq n^5 \leq 5$ and $2 \leq m^5+n^5 \leq 5$.

$Q^5$ in Compound (IX) represents chlorine atom, bromine atom, iodine atom or imidazolyl group, and $Q^5$ in Compound (XII) represents chlorine atom, bromine atom or iodine atom.

$G^4$ in Compound (IX) represents protecting group of hydroxyl group, and preferable examples include trialkylsilyl group such as trimethylsilyl group, allyl group, benzyl group, tetrahydropyranyl group, and the like. $G^5$ in Compound (XI) represents hydrogen atom or a protecting group of hydroxyl group, and preferable examples of the protecting group include trialkylsilyl group such as trimethylsilyl group, allyl group, benzyl group, tetrahydropyranyl group, and the like.

Specific examples of Z, $Z^3$, $Z^4$ and $Z^5$ include the groups of the following formulae:

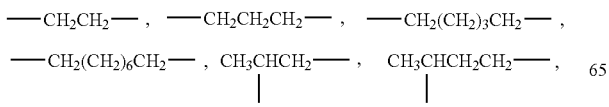

-continued

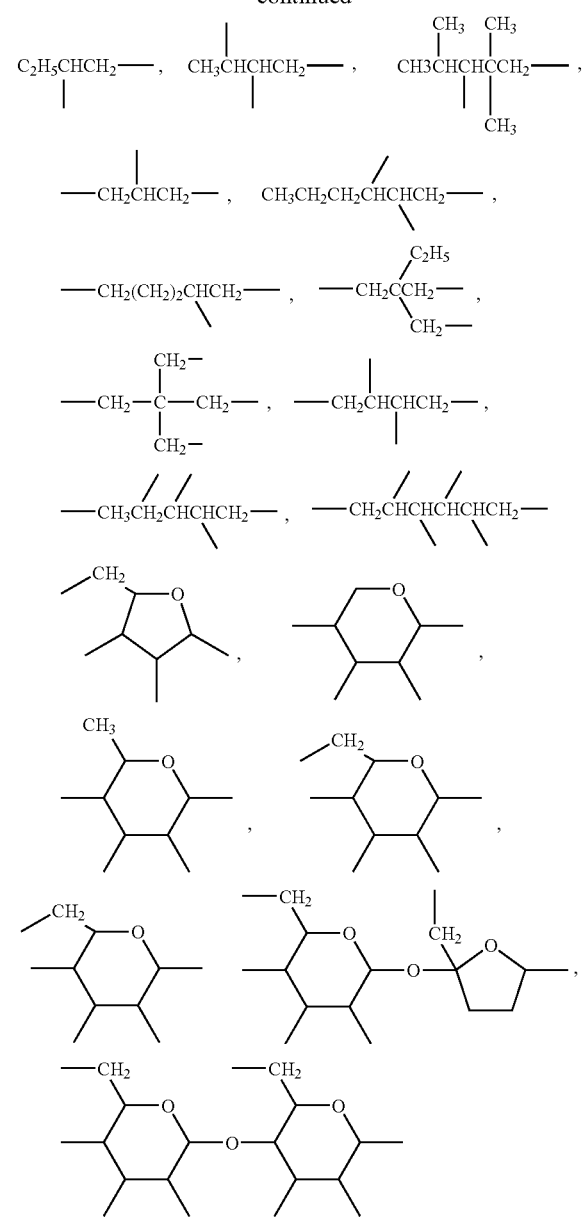

In each of the formulae above, a straight line with an open end shows a bond which is extended from an adjacent carbon atom and which does not specifies a group to be bonded.

Specific examples of A, $A^3$, $A^4$ and $A^5$ include the groups of the following formulae:

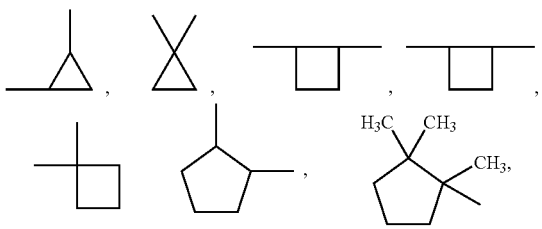

-continued

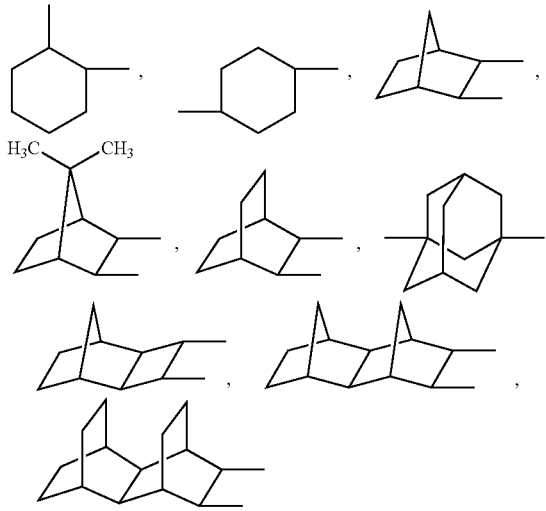

In each of the formulae above, a straight line with an open end shows a bond which is extended from an adjacent carbon atom and which does not specifies a group to be bonded.

Specific examples of W and $W^3$ include the groups of the following formulae:

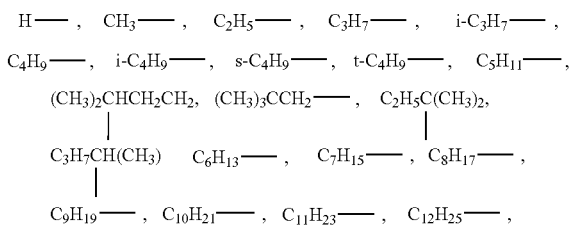

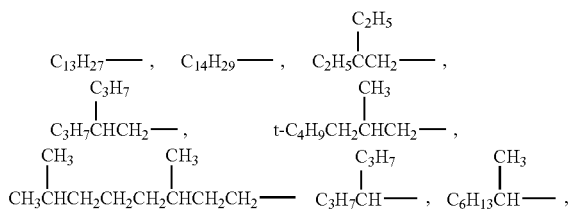

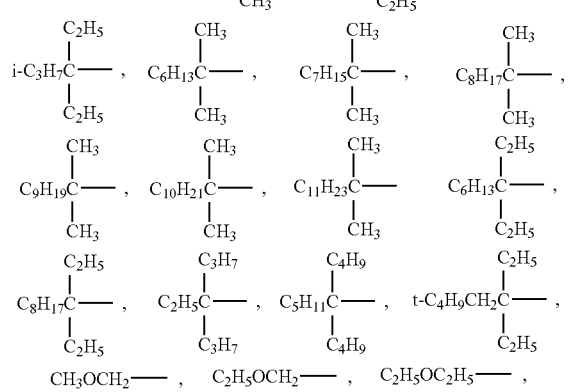

-continued

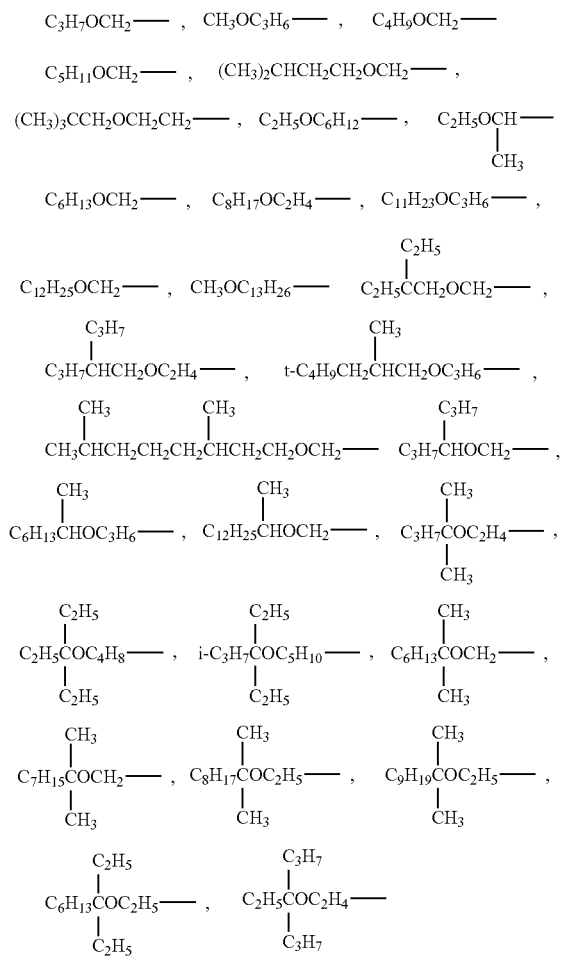

In each of the formulae above, a straight line with an open end shows a bond which is extended from an adjacent carbon atom and which does not specifies a group to be bonded.

Specific examples of the groups of the formulae

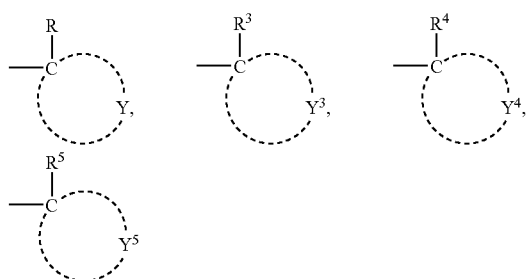

include the following formulae:

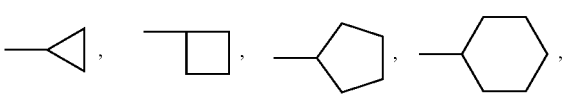

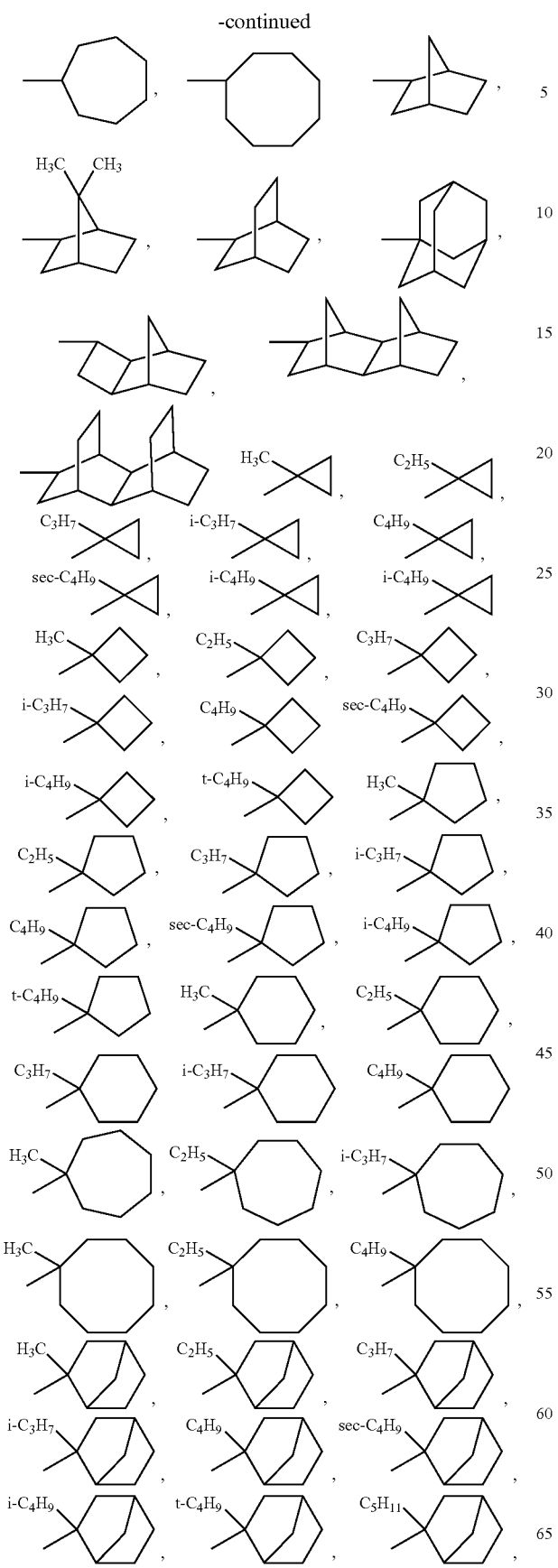
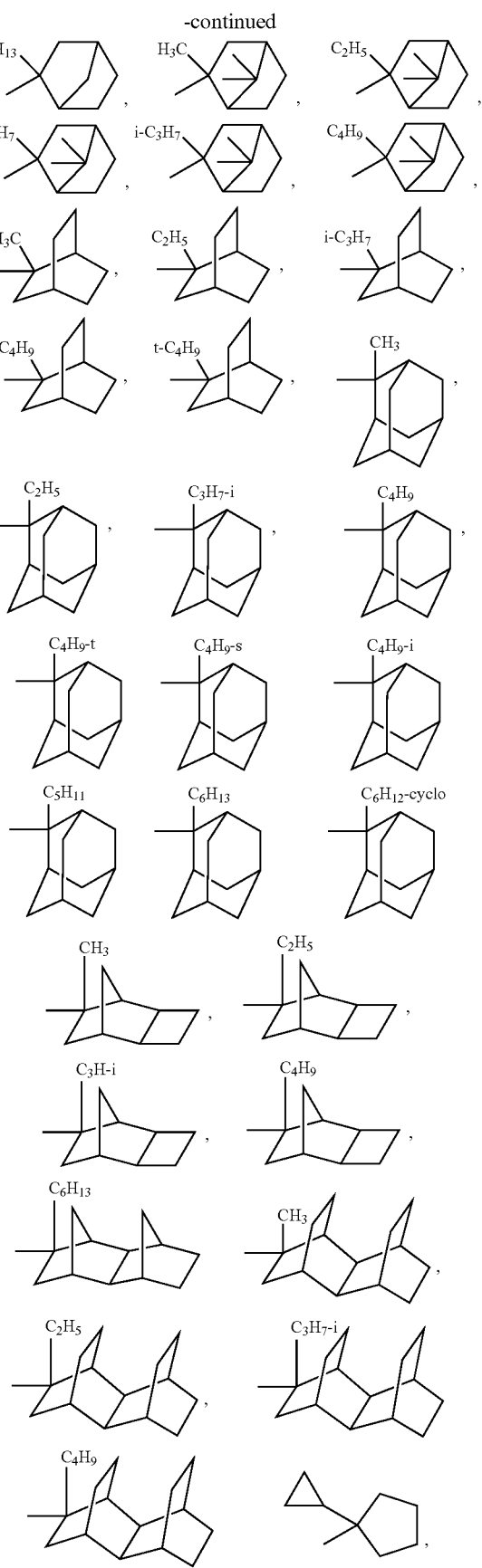

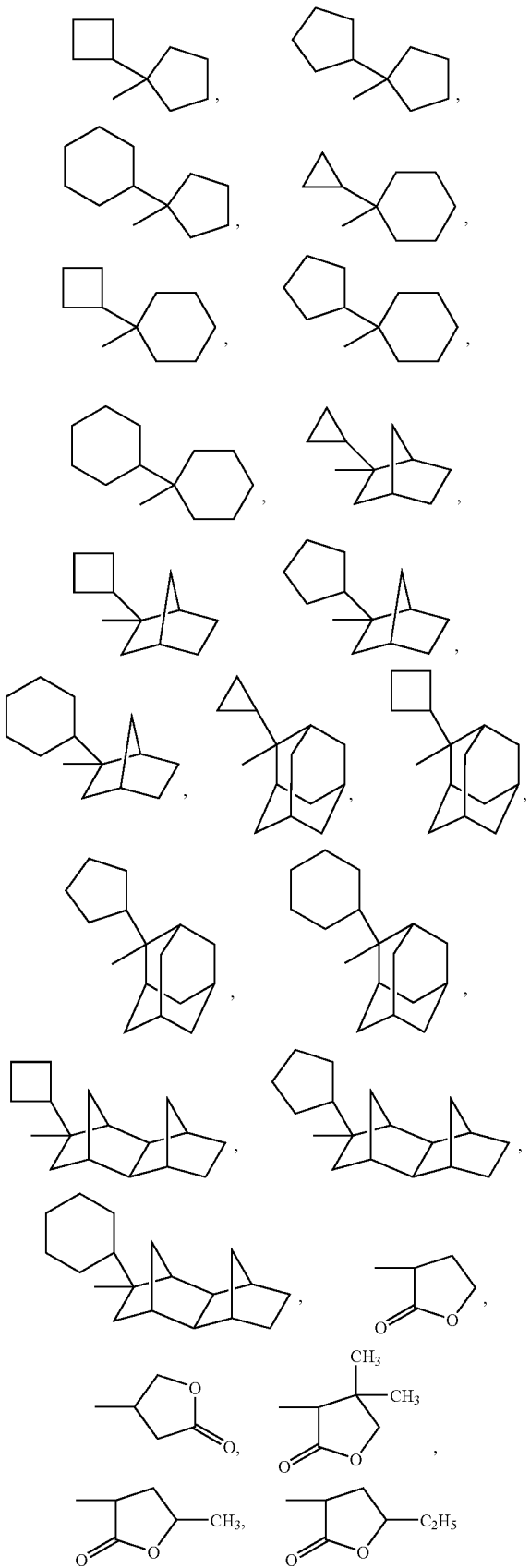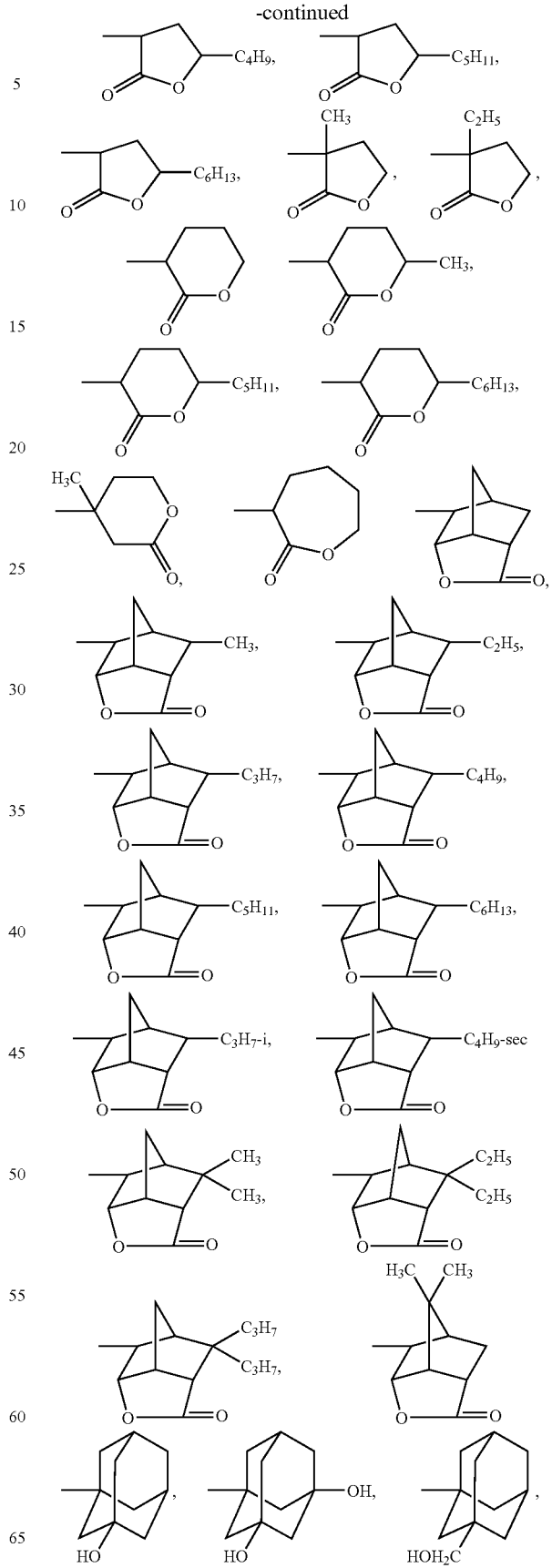

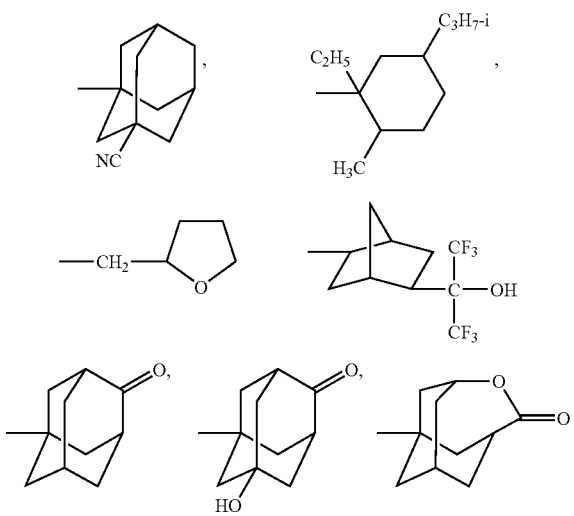

In each of the formulae above, a straight line with an open end shows a bond which is extended from an adjacent carbon atom and which does not specifies a group to be bonded.

Specific examples of X, X³ and X⁵ include the groups of the following formulae:

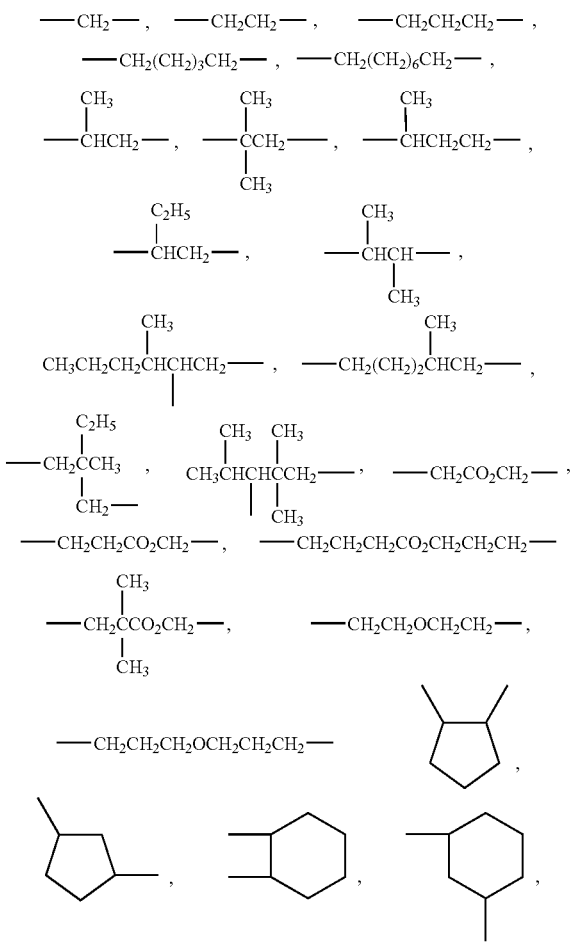

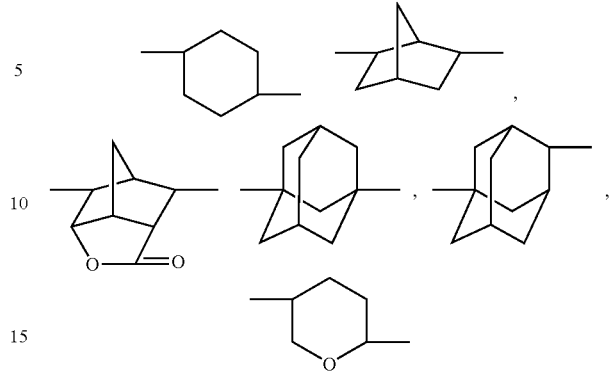

In each of the formulae above, a straight line with an open end shows a bond which is extended from an adjacent carbon atom and which does not specifies a group to be bonded.

Preferred examples of Supracompound (I) include Supracompound (III) and more preferred examples include Supracompound (V).

Ester Derivative (VII) can be obtained by reacting ester derivative with alcohol derivative in the presence of deacidifying agent, and then deprotecting the reaction product.

For example, Ester Derivative (VII') can be obtained by reacting Compound (IX) with Alcohol Derivative (X) in the presence of deacidifying agent, and subjecting the reaction product obtained by the reaction above to deprotection. The amount of Alcohol Derivative (X) is usually 1 to 2 gram equivalents, preferably 1 to 1.5 gram equivalents, per 1 gram equivalent of Compound (IX). The amount of deacidifying agent is usually 1 to 5 gram equivalents, preferably 1 to 3 gram equivalents, per 1 gram equivalent of Compound (IX).

The reaction of Compound (IX) with Alcohol Derivative (X) is usually conducted in an inert solvent such as toluene, tetrahydrofuran, dimethylformamide, dimethylsulfoxide, and the like. Examples of the deacidifying agent include organic base such as amines (e.g. triethylamine, etc.), pyridines (e.g. pyridine, picoline, etc.), and the like, inorganic base such as alkali metal hydroxide (e.g. sodium hydroxide, potassium hydroxide, etc.), alkali metal carbonate (e.g. potassium carbonate, sodium carbonate, etc.), and a mixture thereof.

The reaction can be conducted, for example, by a method of adding a deacidifying agent into a solution of Compound (IX) and Alcohol Derivative (X) in a solvent. Alternatively it can also be conducted by a method of adding Compound (IX) into a solution of Alcohol Derivative (X) and deacidifying agent in a solvent.

The reaction temperature is usually −30 to +200° C., preferably 0 to 150° C. The reaction can be conducted in the presence of phase transfer catalysts such as tetrabutylammonium bromide.

After the reaction, the product can be isolated by conducting conventional method such as neutralization, extraction, crystallization, condensation, and the like. Further, the product can be purified, for example, by recrystallization, chromatography, and the like.

The deprotection reaction can be conducted in a conventional manner. For example, when the protecting group of hydroxyl group is trimethylsilyl group, it can be performed by using desilylating agent such as tetrabutylammonium fluoride. The amount of the desilylating agent is usually 1 to 10 gram equivalents, preferably 1 to 2 gram equivalents, per 1 gram equivalent of the reaction product of Compound (IX) and Alcohol Derivative (X). The reaction is usually conducted in an inert solvent such as toluene, tetrahydrofuran, dimethylformamide, dimethylsulfoxide, and the like. The reaction temperature is usually −30 to +100° C., preferably 0 to 50° C. After the reaction, the product can be isolated by conducting conventional method. Further, the product can be purified, for example, by chromatography, recrystallization, distillation, and the like.

As an alternative method, Ester Derivative (VII) can be obtained by reacting carboxylic acid derivative with alcohol derivative in the presence of deacidifying agent, and then optionally deprotecting the reaction product.

For example, Ester Derivative (VII") can be obtained by reacting Compound (XI) with Compound (XII) in the presence of deacidifying agent, and if $G^5$ is the protecting group of hydroxyl group, further subjecting the reaction product obtained by the reaction above to deprotection.

The amount of Compound (XII) is usually 1 to 2 gram equivalents, preferably 1 to 1.5 gram equivalents, per 1 gram equivalent of Compound (XI). The amount of deacidifying agent is usually 1 to 5 gram equivalents, preferably 1 to 3 gram equivalents, per 1 gram equivalent of Compound (XI).

The reaction of Compound (XI) with Compound (XII) is usually conducted in an inert solvent such as toluene, tetrahydrofuran, dimethylformamide, dimethylsulfoxide, and the like. Examples of the deacidifying agent include organic base such as amines (e.g. triethylamine, etc.), pyridines (e.g. pyridine, picoline, etc.), and the like, inorganic base such as alkali metal hydroxide (e.g. sodium hydroxide, potassium hydroxide, etc.), alkali metal carbonate (e.g. potassium carbonate, sodium carbonate, etc.), and a mixture thereof.

The reaction can be conducted, for example, by a method of adding a deacidifying agent into a solution of Compound (XI) and Compound (XII) in a solvent. Alternatively it can also be conducted by a method of adding Compound (XI) into a solution of Compound (XII) and deacidifying agent in a solvent.

The reaction temperature is usually −30 to +200° C., preferably 0 to 150° C. The reaction can be conducted in the presence of phase transfer catalysts such as tetrabutylammonium bromide.

After the reaction, the product can be isolated by conducting conventional method such as neutralization, extraction, crystallization, condensation, and the like. Further, the product can be purified, for example, by recrystallization, chromatography, and the like.

When $G^5$ is the protecting group of hydroxyl group, the product obtained is subjected to deprotection reaction. The reaction can be conducted in a conventional manner. For example, when the protecting group of hydroxyl group is trimethylsilyl group, it can be performed by using desilylating agent such as tetrabutylammonium fluoride. The amount of the desilylating agent is usually 1 to 10 gram equivalents, preferably 1 to 2 gram equivalents, per 1 gram equivalent of the reaction product of Compound (XI) and Compound (XII). The reaction is usually conducted in an inert solvent such as toluene, tetrahydrofuran, dimethylformamide, dimethylsulfoxide, and the like. The reaction temperature is usually −30 to +100° C., preferably 0 to 50° C. After the reaction, the product can be isolated by conducting conventional method. Further, the product can be purified, for example, by chromatography, recrystallization, distillation, and the like.

Next, resin components constituting the present composition will be explained. The resin used in the present composition contains a structural unit having an acid-labile group and the resin is insoluble or poorly soluble itself in alkali aqueous solution and shows partial dissociation of groups by the action of an acid to become soluble in alkali aqueous solution after the dissociation. The acid-labile group can be selected from conventionally known various groups.

Specifically, various carboxylate groups (—COOR) are mentioned as the acid-labile group, and examples thereof include tertiary alky carboxylate groups such as tert-butyl carboxylate group; acetal type carboxylate groups such as methoxymethyl carboxylate group, ethoxymethyl carboxylate group, 1-ethoxyethyl carboxylate group, 1-isobutoxyethyl carboxylate group, 1-isopropoxyethyl carboxylate group, 1-ethoxypropyl carboxylate group, 1-(2-methoxyethoxy)ethyl carboxylate group, 1-(2-acetoxyethoxy)ethyl carboxylate group, 1-[2-(1-adamantyloxy)ethoxy]ethyl carboxylate group, 1-[2-(1-adamantanecarbonyloxy)ethoxy] ethyl carboxylate group, tetrahydro-2-furyl carboxylate group and tetrahydro-2-pyranyl carboxylate group; alicyclic esters such as isobornyl carboxylate group, 2-alkyl-2-adamantyl carboxylate group, 1-(1-adamantyl)-1-alkylalkyl carboxylate group, and the like.

Monomers to be derived into structural units having such carboxylate group (—COOR) may be (meth)acryl-based monomers such as methacrylates and acrylates, or those obtained by bonding of a carboxylate group to alicyclic monomer such as norbornenecarboxylate, tricyclodecenecarboxylate and tetracyclodecenecarboxylate.

Among the above-mentioned monomers, it is preferable to use those having a bulky group containing alicyclic group such as, for example, 2-alkyl-2-adamantyl group and 1-(1-adamantyl)-1-alkylalkyl group, as the group dissociated by the action of an acid, since excellent resolution is obtained when used in the present composition.

Examples of such monomer containing a bulky group include 2-alkyl-2-adamantyl(meth)acrylate, 1-(1-adamantyl)-1-alkylalkyl(meth)acrylate, 2-alkyl-2-adamantyl 5-norbornene-2-carboxylate, 1-(1-adamantyl)-1-alkylalkyl 5-norbornene-2-carboxylate, 2-alkyl-2-adamantyl α-chloroacrylate, 1-(1-adamantyl)-1-alkylalkyl α-chloroacrylate, and the like.

Particularly when 2-alkyl-2-adamantyl(meth)acrylate or 2-alkyl-2-adamantyl α-chloroacrylate is used as the monomer for the resin component in the present composition, excellent resolution is obtained. Typical examples of such 2-alkyl-2-adamantyl(meth)acrylate and 2-alkyl-2-adamantyl α-chloroacrylate include 2-methyl-2-adamantyl acrylate, 2-methyl-2-adamantyl methacrylate, 2-ethyl-2-adamantyl acrylate, 2-ethyl-2-adamantyl methacrylate, 2-n-butyl-2-adamantyl acrylate, 2-methyl-2-adamantyl α-chloroacrylate, 2-ethyl-2-adamantyl α-chloroacrylate, and the like. When particularly 2-ethyl-2-adamantyl(meth)acrylate or 2-ethyl-2-adamantyl α-chloroacrylate is used for the present composition, balance between sensitivity and heat resistance is excellent. In the present invention, two or more kind of monomers having group dissociated by the action of an acid may be used together, if necessary.

2-alkyl-2-adamantyl(meth)acrylate can usually be produced by reacting 2-alkyl-2-adamantanol or metal salt thereof with an acrylic halide or methacrylic halide.

The resin used for the present composition can also contain, in addition to the above-mentioned structural units having an acid-labile group, other structural units not dissociated or not easily dissociated by the action of an acid. Examples of such other structural units which can be contained include structural units derived from monomers having a free carboxyl group such as acrylic acid and methacrylic acid, structural units derived from aliphatic unsaturated dicarboxylic anhydrides such as maleic anhydride and itaconic anhydride, structural unit derived from 2-norbornene, structural unit derived from (meth)acrylonitrile, and the like.

As it causes no problem on light absorption in the case of KrF exposure, a structural unit derived from hydroxystyrene can be further contained.

Particularly, to contain, in addition to the structural unit having an acid-labile group, further at least one structural unit selected from the group consisting of a structural unit derived from p-hydroxystyrene, a structural unit derived from m-hydroxystyrene, a structural unit derived from 3-hydroxy-1-adamantyl(meth)acrylate, a structural unit derived from 3,5-dihydroxy-1-adamantyl(meth)acrylate, a structural unit derived from (meth)acryloyloxy-γ-butyrolactone having a lactone ring optionally substituted by alkyl group, a structural unit of the following formula (a) and a structural unit of the following formula (b), in the resin in the present composition, is preferable from the standpoint of the adhesiveness of resist to a substrate.

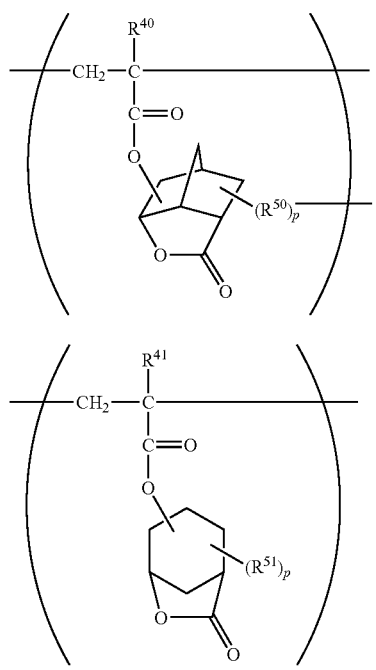

In the formulae (a) and (b), $R^{40}$ and $R^{41}$ each independently represents hydrogen atom, alkyl group having 1 to 4 carbon atoms or perfluoroalkyl group having 1 to 4 carbon atoms, $R^{50}$ and $R^{51}$ each independently represents methyl group, trifluoromethyl group or halogen atom, and p represents an integer of 1 to 3. When p is 2 or 3, each of $R^{50}$ may be the same or different, and each of $R^{51}$ may be the same or different.

3-Hydroxy-1-adamantyl(meth)acrylate and 3,5-dihydroxy-1-adamantyl (meth)acrylate can be produced by, for example, reacting corresponding hydroxyadamantane with (meth)acrylic acid or its acid halide, and they are also commercially available.

Further, (meth)acryloyloxy-γ-butyrolactone can be produced by reacting α- or β-bromo-γ-butyrolactone having a lactone ring optionally substituted by alkyl with acrylic acid or methacrylic acid, or reacting α- or β-hydroxy-γ-butyrolactone having a lactone ring optionally substituted by alkyl with acrylic halide or methacrylic halide.

As monomers to be derived into structural units of the formulae (a) and (b), specifically listed are, for example, (meth)acrylates of alicyclic lactones having hydroxyl group described below, and mixtures thereof, and the like. These esters can be produced, for example, by reacting corresponding alicyclic lactone having hydroxyl group with (meth)acrylic acids, and the production method thereof is described in, for example, JP2000-26446A.

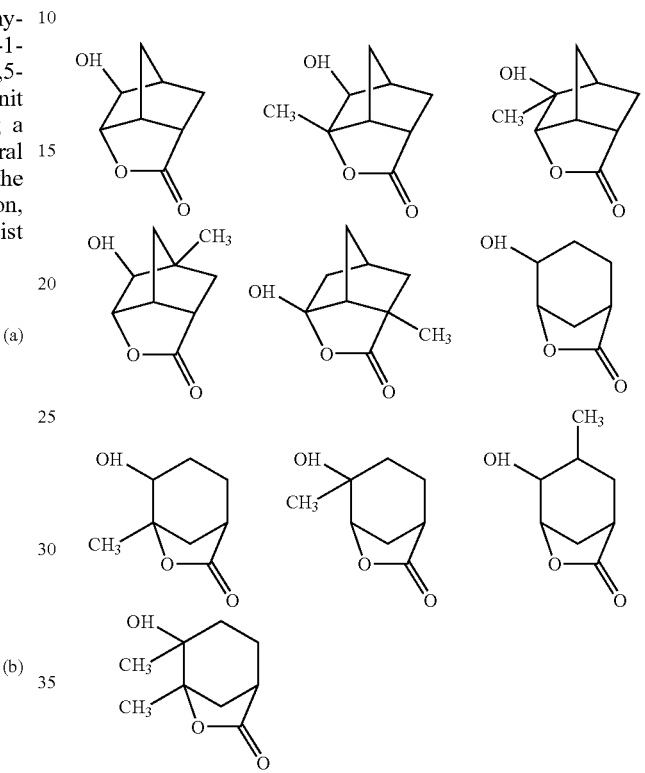

When any of the structural unit derived from 3-hydroxy-1-adamantyl (meth)acrylate, the structural unit derived from 3,5-dihydroxy-1-adamantyl (meth)acrylate, the structural unit derived from α-(meth)acryloyloxy-γ-butyrolactone, the structural unit derived from β-(meth)acryloyloxy-γ-butyrolactone and the structural unit of the formulae (a) and (b) is contained in the resin, not only the adhesiveness of the resist to a substrate is improved, but also the resolution of the resist is improved.

Here, examples of the (meth)acryloyloxy-γ-butyrolactone include α-acryloyloxy-γ-butyrolactone, α-methacryloyloxy-γ-butyrolactone, α-acryloyloxy-β,β-dimethyl-γ-butyrolactone, α-methacryloyloxy-β,β-dimethyl-γ-butyrolactone, α-acryloyloxy-α-methyl-γ-butyrolactone, α-methacryloyloxy-α-methyl-γ-butyrolactone, β-acryloyloxy-γ-butyrolactone, β-methacryloyloxy-γ-butyrolactone, β-methacryloyloxy-α-methyl-γ-butyrolactone and the like.

In the case of KrF excimer laser exposure, sufficient transmittance can be obtained even the structural unit derived from hydroxystyrene is contained in the resin. Specifically, copolymerization resins containing a structural unit derived from p- or m-hydroxystyrene as described below are listed. For obtaining such copolymerization resins, the corresponding (meth)acrylic ester monomer can be radical-polymerized with acetoxystyrene and styrene, and then the reaction mixture can be de-acetylated with an acid.

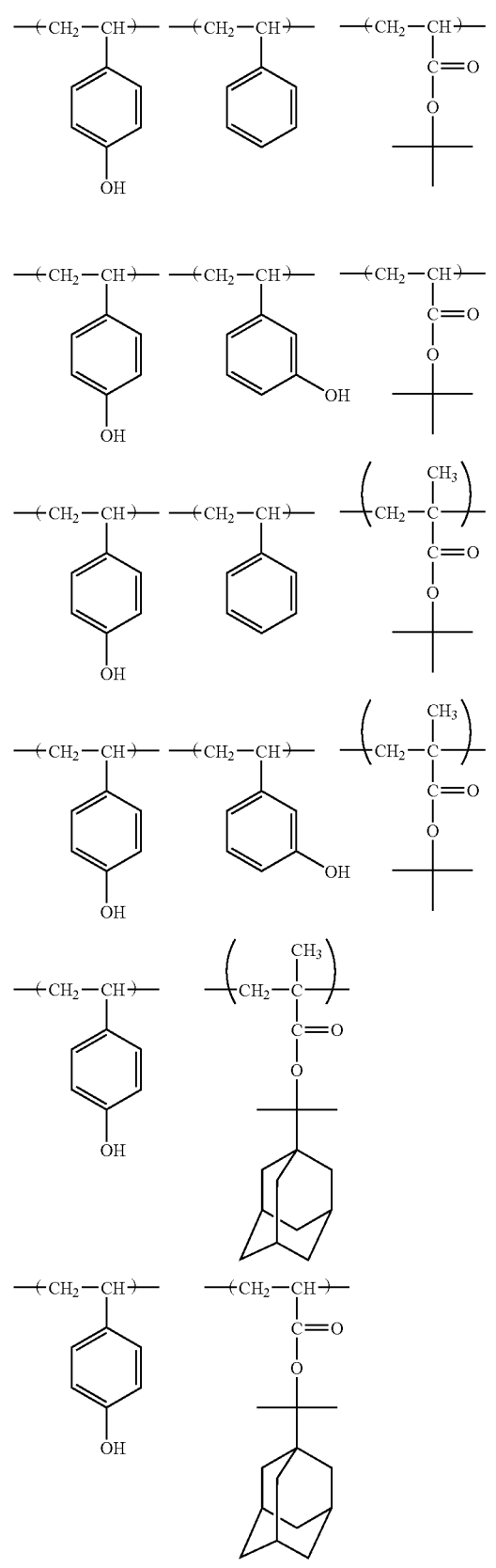
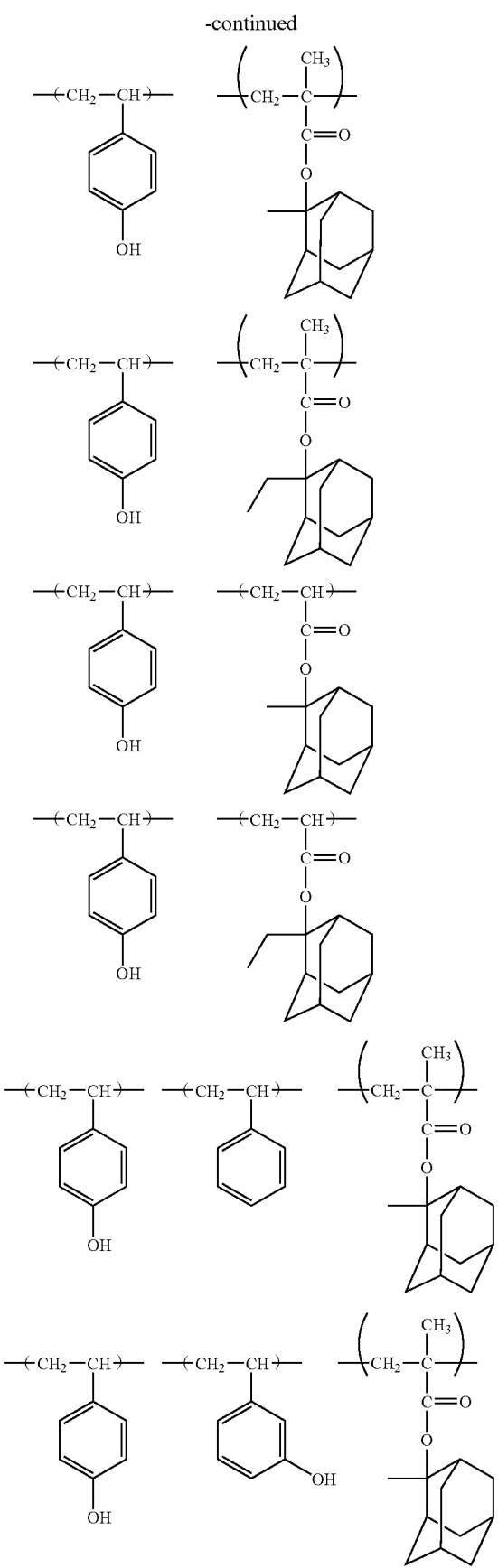

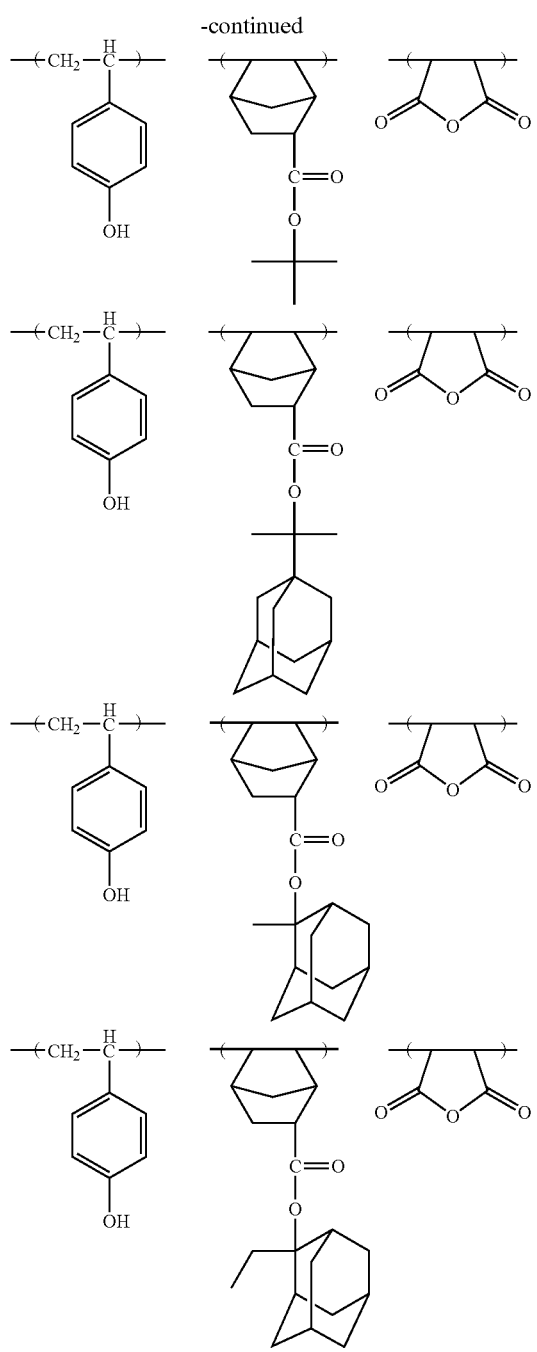

In these cases, it is advantageous from the standpoint of dry etching resistance to contain 2-alkyl-2-adamantyl group or 1-(1-adamantyl)-1-alkylalkyl group as the acid labile group in the resin.

The resin containing a structural unit derived from 2-norbornene shows strong structure because of alicyclic group directly present on its main chain and shows a property that dry etching resistance is excellent. The structural unit derived from 2-norbornene can be introduced into the main chain by radical polymerization using, for example, in addition to corresponding 2-norbornene, aliphatic unsaturated dicarboxylic anhydrides such as maleic anhydride and itaconic anhydride together. The structural unit derived from 2-norbornene is formed by opening of its double bond, and can be represented by the formula (c). The structural unit derived from maleic anhydride and the structural unit derived from itaconic anhydride which are the structural unit derived from aliphatic unsaturated dicarboxylic anhydrides are formed by opening of their double bonds, and can be represented by the formula (d) and the formula (e), respectively.

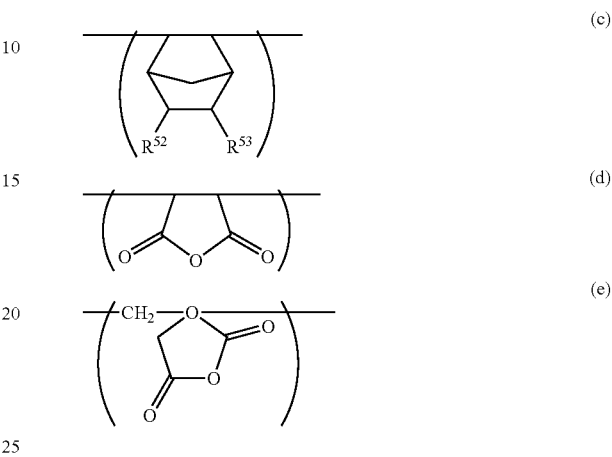

Here, $R^{52}$ and $R^{53}$ in the formula (c) each independently represent hydrogen atom, alkyl group having 1 to 3 carbon atoms, hydroxyalkyl group having 1 to 3 carbon atoms, carboxyl group, cyano group or —COOU group in which U represents alcohol residue, or $R^{52}$ and $R^{53}$ can bond together to form a carboxylic anhydride residue represented by —C(=O)OC(=O)—.

In $R^{52}$ and $R^{53}$, examples of the alkyl group include methyl group, ethyl group, propyl group and isopropyl group, specific examples of hydroxyalkyl group include hydroxymethyl group, 2-hydroxyethyl group and the like.

In $R^{52}$ and $R^{53}$, —COOU group is an ester formed from carboxyl group, and as the alcohol residue corresponding to U, for example, optionally substituted alkyl groups having about 1 to 8 carbon atoms, 2-oxooxolan-3- or -4-yl group and the like are listed, and as the substituent on the alkyl group, hydroxyl group, alicyclic hydrocarbon residues and the like are listed.

Specific examples of —COOU include methoxycarbonyl group, ethoxycarbonyl group, 2-hydroxyethoxycarbonyl group, tert-butoxycarbony group, 2-oxooxalan-3-yloxycarbonyl group, 2-oxooxalan-4-yloxycarbonyl group, 1,1,2-trimethylpropoxycarbonyl group, 1-cyclohexyl-1-methylethoxycarbonyl group, 1-(4-methylcyclohexyl)-1-methylethoxycarbonyl group, 1-(1-adamantyl)-1-methylethoxycarbonyl group and the like.

Specific examples of the monomer used to derive the structural unit represented by the formula (VIII) may include the followings;

2-norbornene,
2-hydroxy-5-norbornene,
5-norbornen-2-carboxylic acid,
methyl 5-norbornen-2-carboxylate,
t-butyl 5-norbornen-2-carboxylate,
1-cyclohexyl-1-methylethyl 5-norbornen-2-carboxylate,
1-(4-methylcyclohexyl)-1-methylethyl 5-norbornen-2-carboxylate,
1-(4-hydroxycyclohexyl)-1-methylethyl 5-norbornen-2-carboxylate,
1-methyl-1-(4-oxocyclohexyl)ethyl 5-norbornen-2-carboxylate, 1-(1-adamantyl)-1-methylethyl 5-norbornen-2-carboxylate,
1-methylcyclohexyl 5-norbornen-2-carboxylate,
2-methyl-2-adamantyl 5-norbornen-2-carboxylate,
2-ethyl-2-adamantyl 5-norbornen-2-carboxylate,
2-hydroxyethyl 5-norbornen-2-carboxylate,
5-norbornen-2-methanol,
5-norbornen-2,3-dicarboxylic acid anhydride, and the like.

The resin used in the present composition preferably contains structural unit(s) having an acid-labile group generally in a ratio of 10 to 80% by mol in all structural units of the resin though the ratio varies depending on the kind of radiation for patterning exposure, the kind of an acid-labile group, and the like.

When the structural units particularly derived from 2-alkyl-2-adamantyl (meth)acrylate or 1-(1-adamantyl)-1-alkylalkyl(meth)acrylate are used as the acid-labile group, it is advantageous that the ratio of the structural units is 15% by mol or more in all structural units of the resin.

When, in addition to structural units having an acid-labile group, other structural units not easily dissociated by the action of an acid, for example, a structural unit derived from 3-hydroxy-1-adamantyl(meth)acrylate, a structural units derived from 3,5-dihydroxy-1-adamantyl(meth)acrylate or α-(meth)acryloyloxy-γ-butyrolactone, a structural units derived from β-(meth)acryloyloxy-γ-butyrolactone, a structural unit of the formula (a) or (b), a structural unit derived from hydroxystyrene, a structural unit of the formula (c), a structural unit derived from maleic anhydride of the formula (d) which is a structural unit derived from an aliphatic unsaturated dicarboxylic anhydride, a structural unit derived from itaconic anhydride of the formula (e) and the like are contained, it is preferable that the sum of these structural units is in the range of 20 to 90% by mol based on all structural units of the resin.

When 2-norbornenes and aliphatic unsaturated dicarboxylic anhydride are used as copolymerization monomer, it is preferable to use them in excess amount in view of a tendency that these are not easily polymerized.

As balance between sensitivity and resolution becomes excellent, it is preferred to use polymer obtained by copolymerizing two kind of monomers having different acid-labile groups as the polymer component of the present composition.

The acid generator, another component of the present composition, is the compound which is decomposed to generate an acid by allowing radioactive ray such as light and electron beam to act on the acid generator itself or a resist composition containing the acid generator. The acid generated from the acid generator acts on the polymer component above, to dissociate acid-labile group present in polymer component.

Such acid generators include, for example, onium salt, organic halogen compounds, sulfone compounds, sulfonate compounds, and the like.

Specific examples thereof include the followings:
diphenyliodonium trifluoromethanesulfonate,
4-methoxyphenylphenyliodinium hexafluoroantimonate,
4-methoxyphenylphenyliodinium trifluoromethanesulfonate,
bis(4-tert-butylphenyl)iodonium tetrafluoroborate
bis(4-tert-butylphenyl)iodonium hexafluorophosphate,
bis(4-tert-butylphenyl)iodonium hexafluoroantimonate
bis(4-tert-butylphenyl)iodonium trifluoromethanesulfonate,
triphenylsulfonium hexafluorophosphate,
triphenylsulfonium hexafluoroantimonate,
triphenylsulfonium trifluoromethanesulfonate,
triphenylsulfonium adamantanemethoxycarbonyldifluoromethylsulfonate,
triphenylsulfonium 1-(3-hydroxymethyladamantane)methoxycarbonyldifluoromethanesulfonate,
triphenylsulfonium 1-(hexahydro-2-oxo-3,5-methano-2H-cyclopenta[b]furan-6-yloxycarbonyl)difluoromethanesulfonate,
triphenylsulfonium 4-oxo-1-adamantyloxycarbonyldifluoromethanesulfonate,
4-methoxyphenyldiphenylsulfonium hexafluoroantimonate,
4-methoxyphenyldiphenylsulfonium trifluoromethanesulfonate,
p-tolyldiphenylsulfonium trifluoromethanesulfonate,
p-tolyldiphenylsulfonium perfluorobutanesulfonate,
p-tolyldiphenylsulfonium perfluorooctanesulfonate,
2,4,6-trimethylphenyldiphenylsulfonium trifluoromethanesulfonate,
4-tert-butylphenyldiphenylsulfonium trifluoromethanesulfonate,
4-phenylthiophenyldiphenylsulfonium hexafluorophosphate,
4-phenylthiophenyldiphenylsulfonium hexafluoroantimonate,
1-(2-naphtholylmethyl)thiolanium hexafluoroantimonate,
1-(2-naphtholylmethyl)thiolanium trifluoromethanesulfonate,
4-hydroxy-1-naphthyldimethylsulfonium hexafluoroantimonate,
4-hydroxy-1-naphthyldimethylsulfonium trifluoromethanesulfonate,
cyclohexylmethyl(2-oxocyclohexyl)sulfonium trifluoromethanesulfonate,
cyclohexylmethyl(2-oxocyclohexyl)sulfonium perfluorobutanesulfonate,
cyclohexylmethyl(2-oxocyclohexyl)sulfonium perfluorooctanesulfonate,
2-oxo-2-phenylethylthiacyclopentanium trifluoromethanesulfonate,
2-oxo-2-phenylethylthiacyclopentanium perfluorobutanesulfonate,
2-oxo-2-phenylethylthiacyclopentanium perfluorooctanesulfonate,
2-oxo-2-phenylethylthiacyclopentanium 4-oxo-1-adamantyloxycarbonyldifluoromethanesulfonate,
2-methyl-4,6-bis(trichloromethyl)-1,3,5-triazine,
2,4,6-tris(trichloromethyl)-1,3,5-triazine
2-phenyl-4,6-bis(trichloromethyl)-1,3,5-triazine,
2-(4-chlorophenyl)-4,6-bis(trichloromethyl)-1,3,5-triazine,
2-(4-methoxyphenyl)-4,6-bis(trichloromethyl)-1,3,5-triazine,
2-(4-methoxy-1-naphthyl)-4,6-bis(trichloromethyl)-1,3,5-triazine,
2-(benzo[d][1,3]dioxolan-5-yl)-4,6-bis(trichloromeythyl)-1,3,5-triazine,
2-(4-methoxystyryl)-4,6-bis(trichloromethyl)-1,3,5-triazine,
2-(3,4,5-trimethoxystyryl)-4,6-bis(trichloromethyl)-1,3,5-triazine,
2-(3,4-dimethoxystyryl)-4,6-bis(trichloromethyl)-1,3,5-triazine,
2-(2,4-dimethoxystyryl)-4,6-bis(trichloromethyl)-1,3,5-triazine,
2-(2-methoxystyryl)-4,6-bis(trichloromethyl)-1,3,5-triazine,
2-(4-butoxystyryl)-4,6-bis(trichloromethyl)-1,3,5-triazine,
2-(4-pentyloxystyryl)-4,6-bis(trichloromethyl)-1,3,5-triazine,
1-benzoyl-1-phenylmethyl p-toluenesulfonate (generally called "benzoin tosylate"),
2-benzoyl-2-hydroxy-2-phenylethyl p-toluenesulfonate (generally called α-methylolbenzoin tosylate), 1,2,3-benzene-tri-yl tris(methanesulfonate),
2,6-dinitrobenzyl p-toluenesulfonate,
2-nitrobenzyl p-toluenesulfonate,
4-nitrobenzyl p-toluenesulfonate,
diphenyl disulfone,
di-p-tolyl disulfone
bis(phenylsulfonyl)diazomethane,
bis(4-chlorophenylsulfonyl)diazomethane,
bis(p-tolylsulfonyl)diazomethane,
bis(4-tert-butylphenylsulfonyl)diazomethane,
bis(2,4-xylylsulfonyl)diazomethane,
bis(cyclohexylsulfonyl)diazomethane,
(benzoyl)(phenylsulfonyl)diazomethane,
N-(phenylsulfonyloxy)succinimide,
N-(trifluoromethylsulfonyloxy)succinimide,
N-(trifluoromethylsulfonyloxy)phthalimide,
N-(trifluoromethylsulfonyloxy)-5-norbornene-2,3-dicarboxyimide,
N-(trifluoromethylsulfonyloxy)naphthalimide,
N-(10-camphorsulfonyloxy)naphthalimide, and the like.

In the present composition, performance deterioration caused by inactivation of acid which occurs due to post exposure delay can be diminished by adding basic compounds, particularly, basic nitrogen-containing organic compounds, for example, amines as a quencher.

Specific examples of such basic nitrogen-containing organic compounds include the ones represented by the following formulae:

[3]

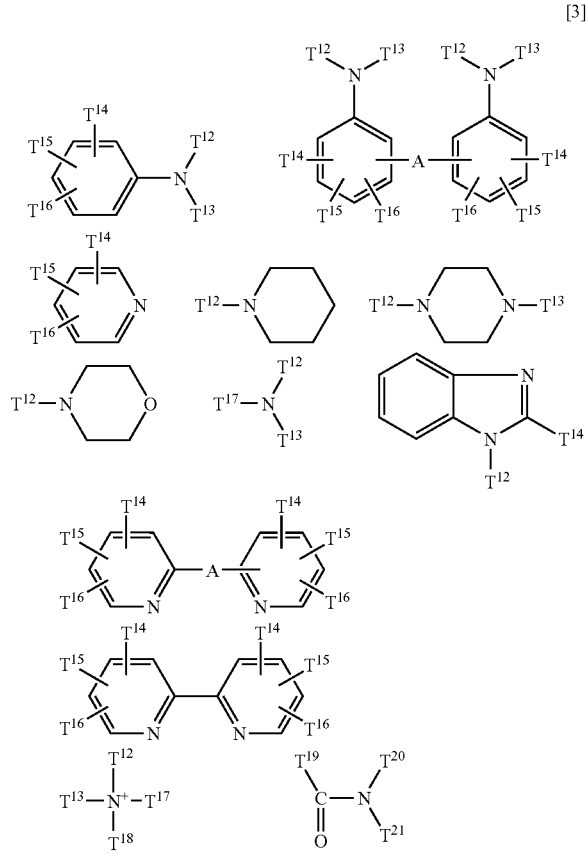

In the formulas, $T^{12}$ and $T^{13}$ each independently represents a hydrogen atom, an alkyl group, a cycloalkyl group or an aryl group. The alkyl group preferably has about 1 to 6 carbon atoms, the cycloalkyl group preferably has about 5 to 10 carbon atoms, and the aryl group preferably has about 6 to 10 carbon atoms. Furthermore, at least one hydrogen atom on the alkyl group, cycloalkyl group or aryl group may each independently be substituted with hydroxyl group, amino group, or alkoxy group having 1 to 6 carbon atoms. At least one hydrogen atom on the amino group may each independently be substituted with alkyl group having 1 to 4 carbon atoms.

$T^{14}$, $T^{15}$ and $T^{16}$ each independently represents a hydrogen atom, an alkyl group, a cycloalkyl group, an aryl group or an alkoxy group. The alkyl group preferably has about 1 to 6 carbon atoms, the cycloalkyl group preferably has about 5 to 10 carbon atoms, the aryl group preferably has about 6 to 10 carbon atoms, and the alkoxy group preferably has about 1 to 6 carbon atoms. Furthermore, at least one hydrogen atom on the alkyl group, cycloalkyl group, aryl group or alkoxy group may each independently be substituted with hydroxyl group, amino group, or alkoxy group having 1 to 6 carbon atoms. At least one hydrogen atom on the amino group may be substituted with alkyl group having 1 to 4 carbon atoms.

$T^{17}$ represents an alkyl group or a cycloalkyl group. The alkyl group preferably has about 1 to 6 carbon atoms, and the cycloalkyl group preferably has about 5 to 10 carbon atoms. Furthermore, at least one hydrogen atom on the alkyl group or cycloalkyl group may each independently be substituted with hydroxyl group, amino group, or alkoxy group having 1 to 6 carbon atoms. At least one hydrogen atom on the amino group may be substituted with alkyl group having 1 to 4 carbon atoms.

In the formulas, $T^{18}$ represents an alkyl group, a cycloalkyl group or an aryl group. The alkyl group preferably has about 1 to 6 carbon atoms, the cycloalkyl group preferably has about 5 to 10 carbon atoms, and the aryl group preferably has about 6 to 10 carbon atoms. Furthermore, at least one hydrogen atom on the alkyl group, cycloalkyl group or aryl group may each independently be substituted with a hydroxyl group, an amino group, or an alkoxy group having 1 to 6 carbon atoms. At least one hydrogen atom on the amino group may each independently be substituted with alkyl group having 1 to 4 carbon atoms.

However, none of $T^{12}$ and $T^{13}$ in the compound represented by the above formula [3] is a hydrogen atom.

A represents alkylene group, carbonyl group, imino group, sulfide group or disulfide group. The alkylene group preferably has about 2 to 6 carbon atoms.

Moreover, among $T^{12}$-$T^{18}$, in regard to those which can be straight-chained or branched, either of these may be permitted.

$T^{19}$, $T^{20}$ and $T^{21}$ each independently represents a hydrogen atom, an alkyl group having 1 to 6 carbon atoms, an aminoalkyl group having 1 to 6 carbon atoms, a hydroxyalkyl group having 1 to 6 carbon atoms or a substituted or unsubstituted aryl group having 6 to 20 carbon atoms, or $T^{19}$ and $T^{20}$ bond to form an alkylene group which forms a lactam ring together with adjacent —CO—N—.

Examples of such compounds include hexylamine, heptylamine, octylamine, nonylamine, decylamine, aniline, 2-, 3- or 4-methylaniline, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, dibutylamine, dipentylamine, dihexylamine, diheptylamine, dioctylamine, dinonylamine, didecylamine, N-methylaniline, piperidine, diphenylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethydipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, N,N-dimethylaniline, 2,6-isopropylaniline, pyridine, 4-methylpyridine, bipyridine, 2,2'-dipyridylamine, di-2-pyridyl ketone, 1,2-di(2-pyridyl)ethane, 1,2-di(4-pyridyl)ethane, 1,3-di(4-pyridyl)propane, 1,2-bis(2-pyridyl)ethylene, 1,2-bis(4-pyridyl)ethylene, 4,4'-dipyridyl sulfide, 4,4'-dipyridyl disulfide, 1,2-bis(4-pyridyl)ethylene, 2,2'-dipicolylamine, 3,3'-dipicolylamine, tetramethylammonium hydroxide, tetraisopropylammonium hydroxide, tetrabutylammonium hydroxide, tetra-n-hexylammonium hydroxide, tetra-n-octylammonium hydroxide, phenyltrimethylammonium hydroxide, 3-trifluoromethylphenyltrimethylammonium hydroxide, (2-hydroxyethyl)trimethylammonium hydroxide (so-called "choline"), N-methylpyrrolidone, and the like.

Furthermore, hindered amine compounds having piperidine skeleton as disclosed in JP-A-H11-52575 can be used as quencher.

It is preferable that the present composition contains polymer component in an amount of about 80 to 99.8% by weight, Supracompound (I) in an amount of 0.1 to 40% by weight and the acid generator in an amount of 0.1 to 20% by weight based on the total amount of polymer component, Supracompound (I) and the acid generator.

When basic compound is used as a quencher, the basic compound is contained preferably in an amount of about 0.001 to 1 part by weight, more preferably in an amount of about 0.01 to 0.3 part by weight based on 100 parts by weight of polymer component.

The present composition can contain, if necessary, various additives in small amount such as a sensitizer, solution suppressing agent, other polymers, surfactant, stabilizer, dye and the like, as long as the effect of the present invention is not prevented.

The present composition is usually in the form of a resist liquid composition in which the aforementioned ingredients are dissolved in a solvent, and the resist liquid composition is to be applied onto a substrate such as a silicon wafer by a conventional process such as spin coating. The solvent used here is sufficient to dissolve the aforementioned ingredients, have an adequate drying rate, and give a uniform and smooth coat after evaporation of the solvent and, hence, solvents generally used in the art can be used. In the present invention, the total solid content means total content exclusive of solvents.

Examples thereof include glycol ether esters such as ethyl Cellosolve acetate, methyl Cellosolve acetate and propylene glycol monomethyl ether acetate; ethers such as di(ethylene glycol)dimethyl ether; esters such as ethyl lactate, butyl lactate, amyl lactate and ethyl pyruvate and the like; ketones such as acetone, methyl isobutyl ketone, 2-heptanone and cyclohexanone; cyclic esters such as γ-butyrolactone, and the like. These solvents can be used each alone or in combination of two or more.

A resist film applied onto the substrate and then dried is subjected to exposure for patterning, then heat-treated for facilitating a deblocking reaction, and thereafter developed with an alkali developer. The alkali developer used here may be any one of various alkaline aqueous solutions used in the art, and generally, an aqueous solution of tetramethylammonium hydroxide or (2-hydroxyethyl)trimethylammonium hydroxide (commonly known as "choline") is often used.

It should be construed that embodiments disclosed here are examples in all aspects and not restrictive. It is intended that the scope of the present invention is determined not by the above descriptions but by appended claims, and includes all variations of the equivalent meanings and ranges to the claims.

The present invention will be described more specifically by way of examples, which are not construed to limit the scope of the present invention. The "%" and "part(s)" used to represent the content of any component and the amount of any material used in the following examples are on a weight basis unless otherwise specifically noted. The weight-average molecular weight of any material used in the following examples is a value found by gel permeation chromatography using styrene as a standard reference material.

EXAMPLE 1

Synthesis of PECHOM

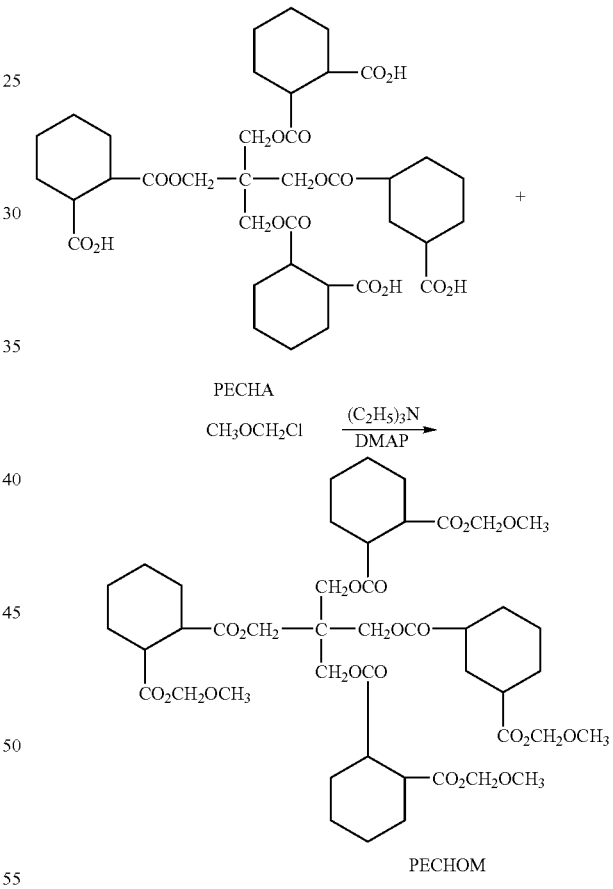

To a solution consisting of 110 g of tetracarboxylic acid (abbreviated to "PECHA") above, which is described in JP2000-302839 A, 59 g of chloromethyl methyl ether and 500 ml of N,N-dimethylformamide (abbreviated to "DMF"), a solution consisting of 118 g of triethylamine (abbreviated to "TEA"), 4.4 g of dimethylaminopyridine (abbreviated to "DMAP") and 300 ml of DMF was added dropwise at 5 to 10° C. for 2.5 hours. After stirred overnight, the reaction mixture was diluted by water, and extracted with ethyl acetate. The organic layer obtained was washed with water, with sodium bicarbonate solution, and then with water. After dried with anhydrous magnesium sulfate, the organic solution was concentrated. The crude product obtained (132 g) was purified by silica gel column chromatography (developer: heptane/ethyl acetate) to obtain 102 g of tetracarboxylate (abbreviated to "PECHOM").

$^1$H NMR(CDCl$_3$):d1.3-1.65 (16H, cyclohexyl), 1.65-2.15 (16H, cyclohexyl), 2.75-3.0 (8H, cyclohexyl), 3.45 (12H, s, CH$_3$), 4.0-4.2 (8H, CH$_2$), 5.1-5.35 (8H, CH$_2$) $^{13}$C NMR (CDCl$_3$):d23.32 (cyclohexyl), 23.96 (cyclohexyl), 25.73 (cyclohexyl), 26.49 (cyclohexyl), 42.04 (quaternary carbon), 42.43 (cyclohexyl), 42.56 (cyclohexyl), 57.52 (CH$_3$), 62.42 (CH$_2$), 90.44 (CH$_2$), 172.97 (C=O), 173.01 (C=O) FD-MS: 930 (M+H)$^+$(C$_{45}$H$_{68}$O$_{20}$=929.01)

EXAMPLE 2

Synthesis of PECH-AMAD ing of 14.5 g of 2-methyl-2-adamantyl chloroacetate (abbreviated to "CAMAD") and 20 g of DMF was added at room temperature. To the mixture, 3.3 g of potassium iodide was added, and the added mixture was stirred overnight at room temperature overnight. After the stirring, the reaction mixture was diluted with water, then extracted with ethyl acetate. The organic layer obtained was washed with water, dried and decolorized with anhydrous magnesium sulfate and activated carbon, then concentrated. The crude product obtained (21.3 g) was purified by silica gel column chromatography (developer: heptane/ethyl acetate) to obtain 15.5 g of tetracarboxylate (abbreviated to "PECH-AMAD").

$^1$H NMR (CDCl$_3$):d1.3-1.65 (16H, cyclohexyl), 1.55-1.57 (16H, adamantyl), 1.62 (12H, s, CH$_3$), 1.70-1.72 (8H, adamantyl), 1.80 (8H, adamantyl), 1.70-1.89 (16H, adamantyl), 1.75-2.11 (16H, cyclohexyl), 1.95-2.03 (16H, adamantyl), 2.27-2.30 (8H, adamantyl), 2.78 (4H, m, cyclohexyl), 2.98 (4H, m, cyclohexyl), 4.06 (8H, s, methylene), 4.41-4.71 (8H, m, methylene) $^{13}$C NMR(CDCl$_3$):d22.14 (CH$_3$), 23.10 (cyclohexyl), 23.89 (cyclohexyl), 25.58 (cyclohexyl), 26.42 (cyclohexyl and adamantyl), 27.11 (adamantyl), 32.76 and 32.78 (adamantyl), 36.00 and 36.11 (adamantyl), 37.91 (adamantyl), 41.90 (quaternary carbon), 41.94 (cyclohexyl), 42.47 (cyclohexyl), 60.80(CH$_2$), 62.26 (CH$_2$), 166.38 (C=O), 172.60 (C=O), 172.77 (C=O) GPC-MS:1617(M+K)$^+$ (C$_{89}$H$_{124}$O$_{24}$=1577.92)

EXAMPLE 3

Synthesis of PECH-AHAD

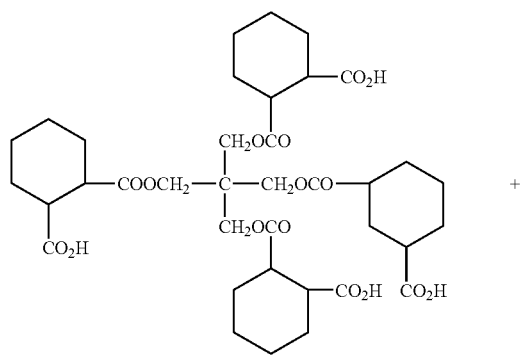

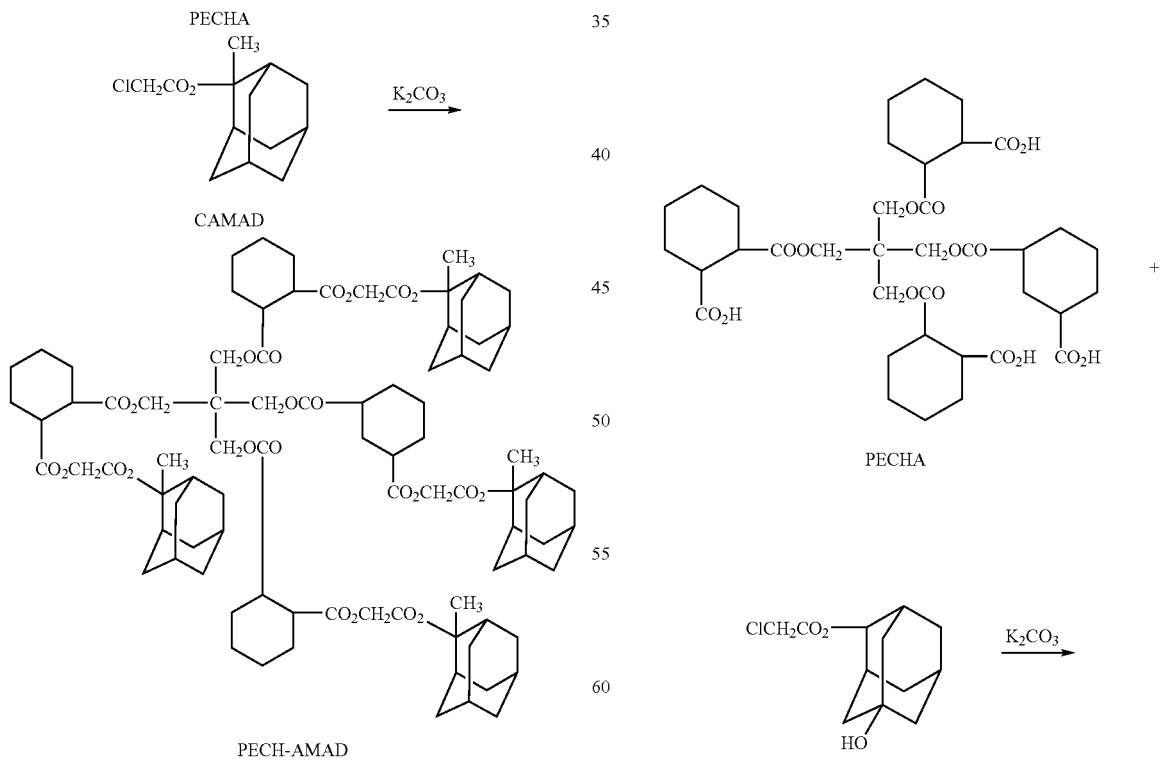

A solution was prepared by adding 11.0 g of potassium carbonate to a mixture obtained by dissolving 10.0 g of PECHA in 100 g of DMF. To the solution, a solution consist- -continued

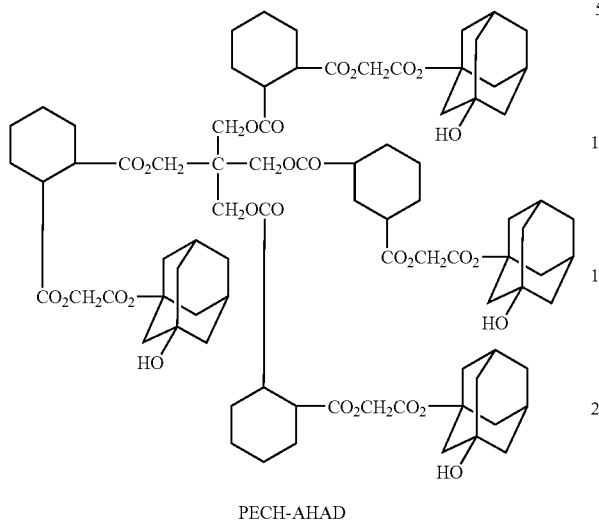

PECH-AHAD

A solution was prepared by adding 5.5 g of potassium carbonate to a mixture obtained by dissolving 5.0 g of PECHA in 30 g of DMF. To the solution, a solution consisting of 6.5 g of 3-hydroxyadamantyl chloroacetate (abbreviated to "CAHAD") and 32.5 g of DMF was added at room temperature. To the mixture, 1.65 g of potassium iodide was added, and the added mixture was stirred at 40° C. for 2 hours. After cooling, the reaction mixture was diluted with water, then extracted with ethyl acetate. The organic layer obtained was washed with water, dried with anhydrous magnesium sulfate, and then concentrated. The crude product obtained (12.0 g) was purified by silica gel column chromatography (developer: ethyl acetate) to obtain 7.7 g of tetracarboxylate (abbreviated to "PECH-AHAD").

$^1$H NMR (CDCl$_3$):d1.35-1.60 (16H, cyclohexyl), 1.48-1.56 (8H, adamantyl), 1.65-1.71 (16H, adamantyl), 1.71-2.13 (16H, cyclohexyl), 2.02 (16H, adamantyl), 2.11 (8H, adamantyl), 2.31 (8H, adamantyl), 2.48 (4H, OH), 2.75 (4H, m, cyclohexyl), 3.01 (4H, m, cyclohexyl), 4.07 (8H, s, methylene), 4.38-4.62 (8H, m, methylene) $^{13}$C NMR (CDCl$_3$):d23.01 (adamantyl), 23.98 (cyclohexyl), 25.45 (cyclohexyl), 26.57 (cyclohexyl), 31.04 (adamantyl), 34.50 (cyclohexyl), 39.78と 39.80 (adamantyl), 41.92と42.54 (cyclohexyl), 43.65 (adamantyl), 48.74 (adamantyl), 60.98 (CH$_2$), 62.58 (CH$_2$), 69.93 and 69.95 (adamantyl), 82.84 (adamantyl), 166.46 (C=O), 172.65 (C=O), 173.00 (C=O) GPC-MS:1625(M+K)$^+$ (C$_{85}$H$_{116}$O$_{28}$=1585.81)

EXAMPLE 4

Synthesis of PECH-ANL

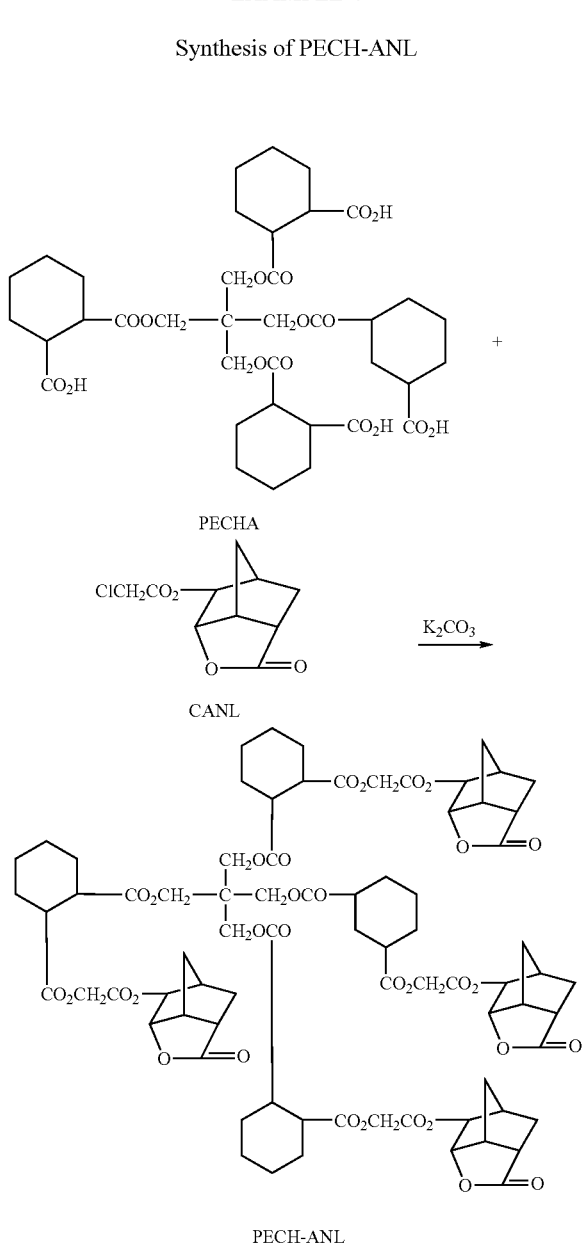

A solution was prepared by adding 11.0 g of potassium carbonate to a mixture obtained by dissolving 10.0 g of PECHA in 60 g of DMF. To the solution, a solution consisting of 12.3 g of hexahydro-2-oxo-3,5-methano-2H-cyclopenta[b]furan-6-yl chloroacetate (abbreviated to "CANL") and 40 g of DMF was added at room temperature. To the mixture, 3.3 g of potassium iodide was added, and the added mixture was stirred at room temperature overnight. After the stirring, ethyl acetate and water was added to the reaction mixture, then the product was extracted from the mixture with ethyl acetate. The organic layer was washed with ion-exchanged water, dried with anhydrous magnesium sulfate, then concentrated under reduced pressure to obtain 19.0 g of tetracarboxylate (abbreviated to "PECH-ANL").

$^1$H NMR (CDCl$_3$):d1.35-1.60 (16H, cyclohexyl), 1.64 and 1.66 (4H, norbornanelactone), 1.72 and 1.75 (4H, norbornanelactone), 1.75-2.12 (16H, cyclohexyl), 1.99 and 2.01 (4H, norbornanelactone), 2.03-2.06 (4H, norbornanelactone), 2.54-2.76 (4H, norbornanelactone), 2.57 (4H, m, norbornanelactone), 2.77 (4H, m, cyclohexyl), 3.03 (4H, m, cyclohexyl), 3.22 (4H, m, norbornanelactone), 4.06 (8H, m, methylene), 4.56 (4H, m, norbornanelactone), 4.63 (4H, s, norbornanelactone), 4.51-4.74 (8H, m, methylene) $^{13}$C NMR (CDCl$_3$):d22.78 and 22.86 (cyclohexyl), 23.78 and 23.86 (cyclohexyl), 25.24&25.36 (cyclohexyl), 26.40 and 26.50 (cyclohexyl)31.24 (norbornanelactone), 33.86 (norbornanelactone), 37.72 (norbornanelactone), 40.94 and 40.96 (norbornanelactone), 41.65 and 31.68 (cyclohexyl), 41.76 (quaternary carbon), 42.33 and 42.38 (cyclohexyl), 44.72 (norbornanelactone), 60.33 (CH$_2$), 62.30 (CH$_2$), 79.40 (norbornanelactone), 80.09 (norbornanelactone), 166.44 (C=O), 172.60 (C=O), 172.70 (C=O), 172.29 (C=O) GPC-MS: 1569.5(M+K)$^+$ (C$_{77}$H$_{92}$O$_{32}$=1529.54)

EXAMPLE 5

Syntheses of PECH-3-AMAD-ANL and PECH-2-AMAD-2-ANL

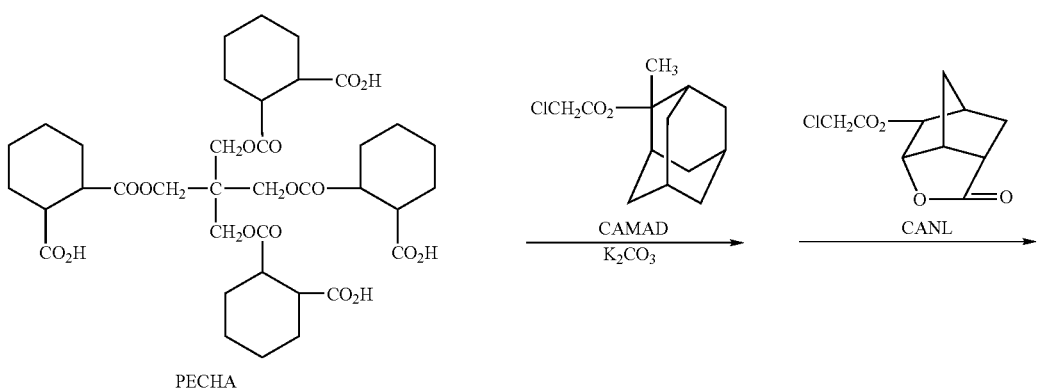

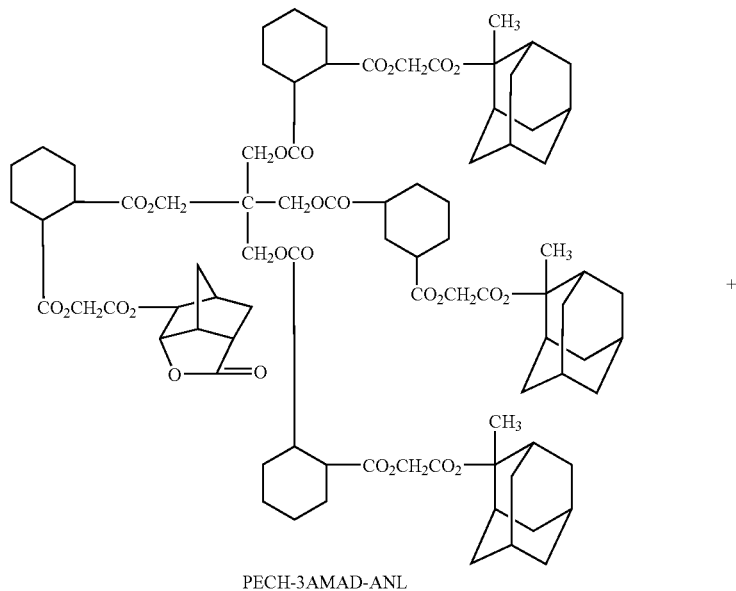

PECH-3AMAD-ANL

-continued

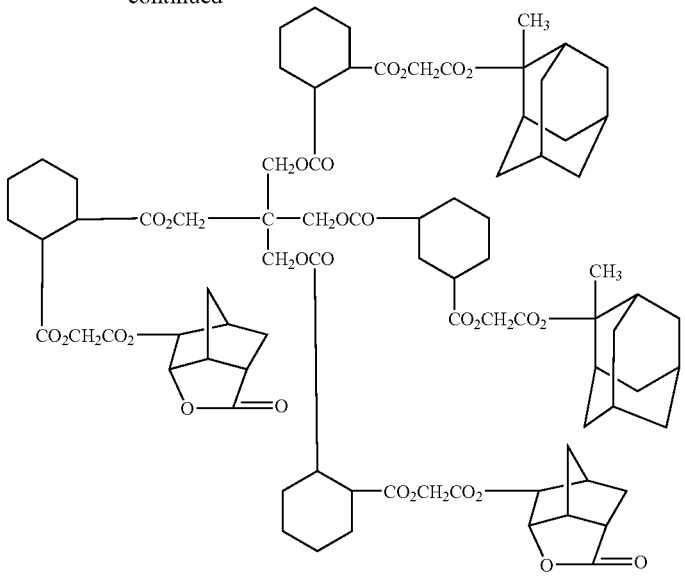

PECH-2AMAD-2ANL

A solution was prepared by adding 8.26 g of potassium carbonate to a mixture obtained by dissolving 10.0 g of PECHA in 60 g of DMF. To the solution, a solution consisting of 10.78 g of CAMAD and 40 g of DMF was added at room temperature. To the mixture, 2.48 g of potassium iodide was added, and the added mixture was stirred at room temperature for 2 hours. To the mixture, CANL was added, and the added mixture was stirred at room temperature overnight. After the stirring, ethyl acetate and water was added to the reaction mixture, then the product was extracted from the mixture with ethyl acetate. The organic layer was washed with ion-exchanged water, dried with anhydrous magnesium sulfate, then concentrated under reduced pressure. The product obtained was purified by silica gel column chromatography to obtain 3.81 g of tetracarboxylate3/1 (abbreviated to "PECH-3-AMAD-ANL") and 4.14 g of tetracarboxylate2/2 (abbreviated to "PECH-2-AMAD-2-ANL").

GPC-MS: (PECH-3-AMAD-ANL) 1603.5(M+K)$^+$ ($C_{86}H_{124}O_{26}$=1565.83) GPC-MS: (PECH-2-AMAD-2-ANL) 1591.5(M+K)$^+$ ($C_{83}H_{108}O_{28}$=1553.73)

EXAMPLE 6

Synthesis of GLUCH-5AMAD

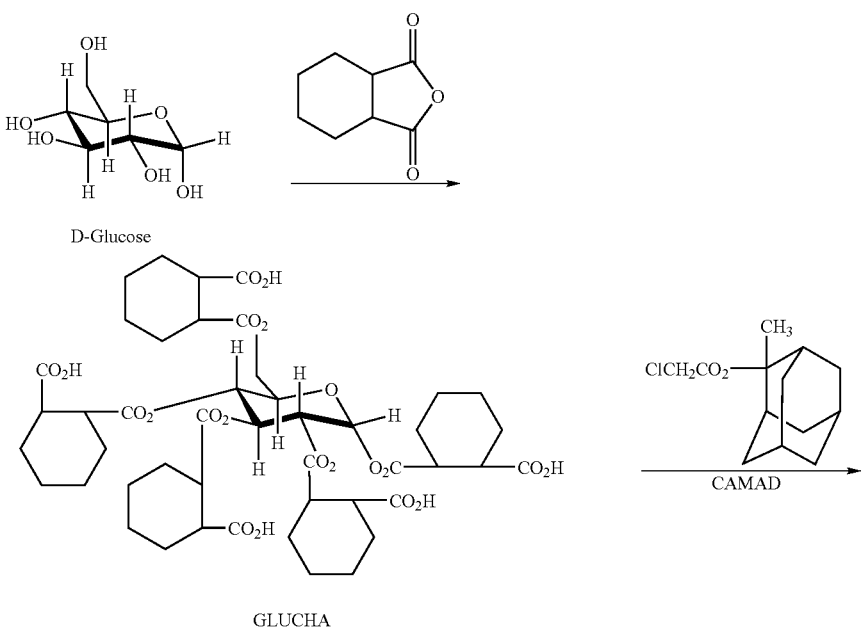

GLUCHA

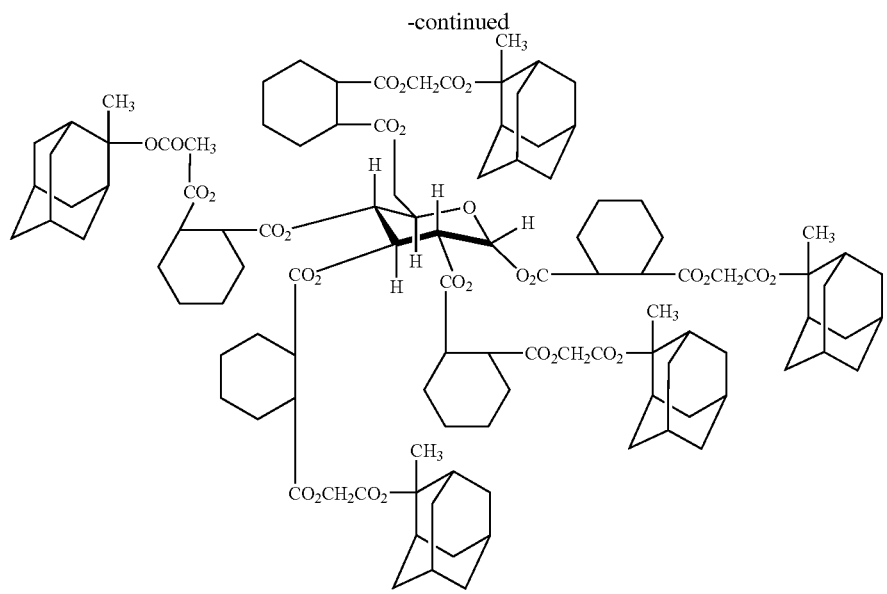

GLUCH-5AMAD

To a mixture of 20.0 g of D-glucose, 3.4 g of 4-(N,N-dimethylamino)pyridine, 68.0 g of TEA and 440 g of THF, a solution of 86.0 g of cis-1,2-cyclohexanedicarboxylic anhydride and 88 g of THF was added with stirring at room temperature, then the added mixture was stirred for 3 days. After the stirring, the solvent was removed from the resulting mixture under reduced pressure. To the concentrate, 600 g of chloroform and 300 g of ion-exchanged water was added, and was neutralized with hydrochloric acid. The neutralized organic layer was separated, washed with ion-exchanged water, and dried with anhydrous magnesium sulfate. Then the solvent was removed from the dried organic layer to obtain 160.1 g of crude pentakis-D-glucose (2-carboxycyclohexyl) carboxylate (abbreviated to "GLUCHA").

A solution was prepared by adding 10.36 g of potassium carbonate to a mixture obtained by dissolving 9.50 g of GLUCHA in 70 g of DMF. To the solution, a solution consisting of 13.62 g of CAMAD and 40 g of DMF was added at room temperature. To the mixture, 3.11 g of potassium iodide was added, and the added mixture was stirred at room temperature overnight. After the stirring, ethyl acetate and ion-exchanged water was added to the reaction mixture, then the product was extracted from the mixture with ethyl acetate. The organic layer was washed with ion-exchanged water, dried with anhydrous magnesium sulfate, then concentrated under reduced pressure. The product obtained was purified by silica gel column chromatography to obtain 2.68 g of pentacarboxylate (abbreviated to "GLUCH-5AMAD").

GPC-MS: (GLUCH-5 AMAD) 2019.7(M+K)$^+$ ($C_{111}H_{152}O_{31}$=1982.38)

EXAMPLE 7

Synthesis of GLUCH-4-AMAD

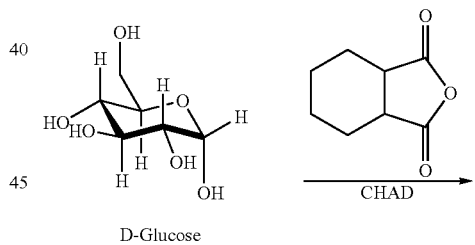

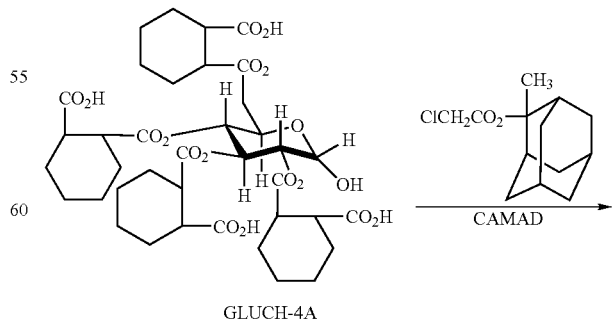

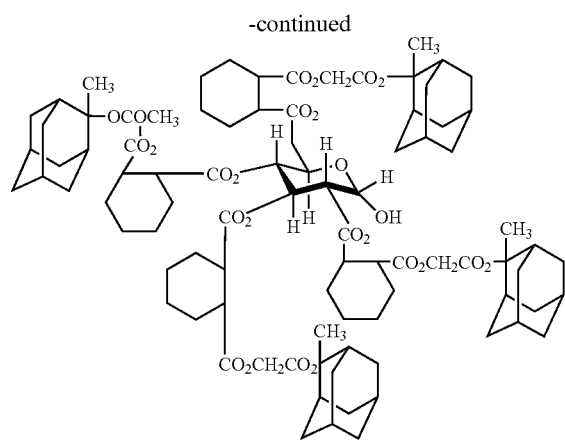
GLUCH-4AMAD
The experiment was conducted in the same manner as in Example 6 except that the amount of cis-1,2-cyclohexanedicarboxylic anhydride and of CAMAD were changed to obtain GLUCH-4 AMAD.
GPC-MS: (GLUCH-4 AMAD) 1659.7(M+K)$^+$ ($C_{90}H_{124}O_{26}$=1621.93)
EXAMPLE 8
Synthesis of PENB04 AMAD
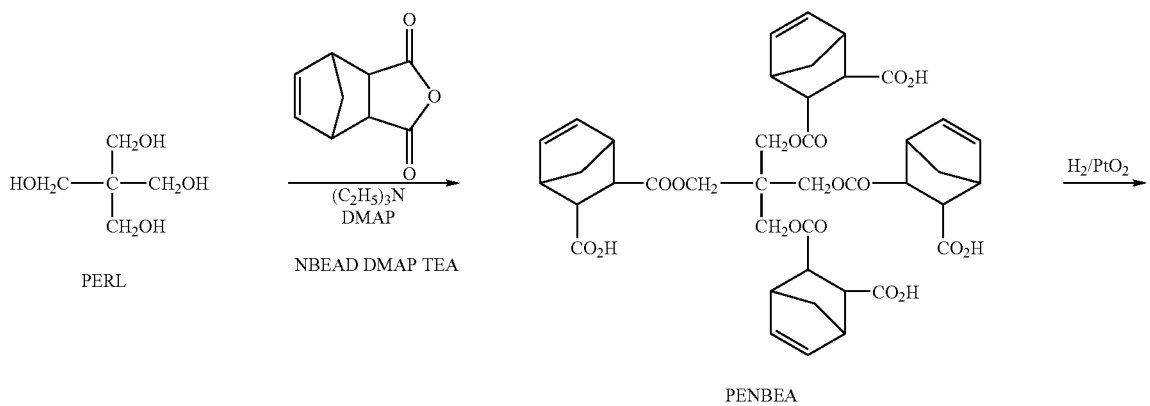
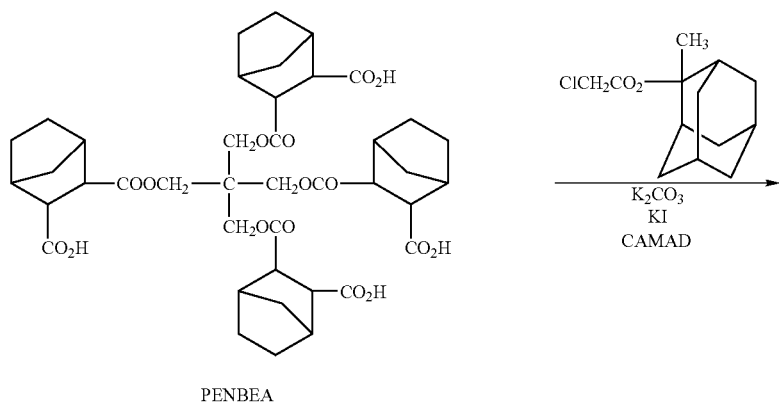

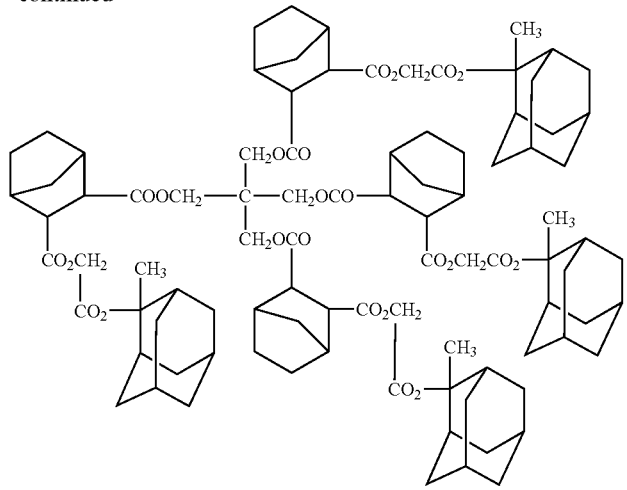

PENB-4AMAD

After suspending 20.0 g of pentaerythritol in 444 g of THF, 3.6 g of DMAP and 74.3 g of TEA were added to the suspension. To the added suspension, a solution of 97.4 g of 5-norbornen-2,3-dicarboxylic anhydride (abbreviated to "NBEAD") and 88.8 g of THF was added dropwise. After the mixture was stirred overnight, the stirring was maintained at 40° C. for 3 hours. The reaction mixture was diluted with dilute hydrochloric acid. The diluted mixture was extracted with chloroform, then the organic layer obtained was dried with anhydrous magnesium sulfate. Chloroform was evaporated from the organic layer to obtain 122.4 g of tetracarboxylic acid (abbreviated to "PENBEA").

110 g of PENBEA obtained above was dissolved in 552 g of methanol, and was catalytically hydrogenated using 3.16 g of platinum dioxide. After absorbing preliminarily determined amount of hydrogen, the catalyst was filtrated off. The filtrate was concentrated to obtain 109.7 g of tetracarboxylic acid (abbreviated to "BENBA").

LC-MS: (PENBA) 839.2(M+K)$^+$ ($C_{41}H_{52}O_{16}$=800.84)

16.0 g of PENBA obtained above was dissolved in 143.2 g of DMF. 21.34 g of CAMAD, 16.57 g of potassium carbonate and 0.33 g of potassium carbonate were added thereto, and the mixture was stirred at 40° C. for 4 hours. The mixture was further stirred at room temperature overnight. The resulting mixture was diluted with water, and then was extracted with ethyl acetate. The organic layer was washed with water, dried with anhydrous magnesium sulfate, and then concentrated. The concentrate was purified by silica gel column chromatography to obtain 9.1 g of tetraester compound (abbreviated to "PENB-4 AMAD"). (Melting Point: 97-98° C.)

$^1$H NMR(CDCl$_3$):d1.45-2.10(72H, adamantyl and norbornyl), 1.63(12H, CH$_3$), 2.29(8H, m, adamantyl), 2.55-2.61 (8H, norbornyl), 2.97-3.13(8H, norbornyl), 3.61(8H, s, methylene), 4.39-4.67(8H, m, methylene) $^{13}$C NMR (CDCl$_3$): d22.13 (CH$_3$), 23.78 and 23.82 (norbornyl), 26.42 (adamantyl), 27.1 (adamantyl), 32.79 (adamantyl), 34.34 (adamantyl), 36.09 (adamantyl), 37.93 (adamantyl), 39.73 (norbornyl), 40.07&40.14 (norbornyl), 40.23 (norbornyl), 46.30 and 6.42 (norbornyl), 51.07 (CH$_2$), 60.73 (CH$_2$), 88.70 (adamantyl), 166.41 (C=O), 171.68 (C=O), 172.63 (C=O) LC-MS: (PENB-4 AMAD)1663.6(M+K)$^+$ ($C_{93}H_{124}O_{24}$=1625.97)

EXAMPLE 9

Synthesis of PENB-3 AMAD

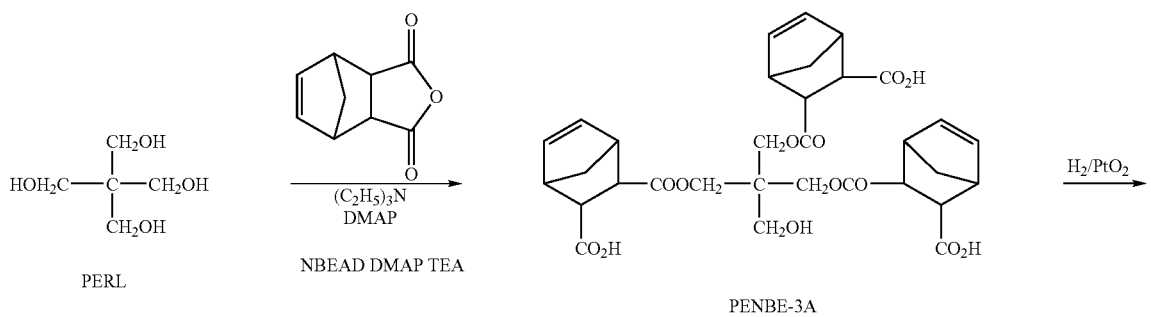

-continued

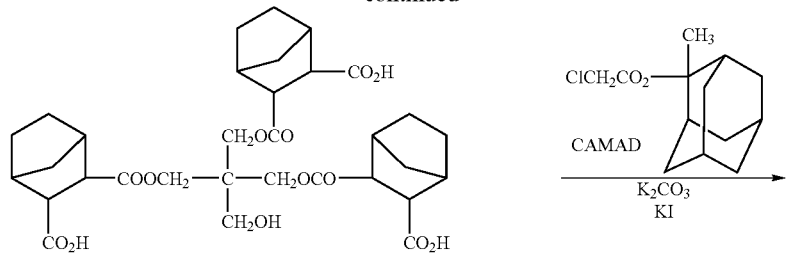

PENB-3A

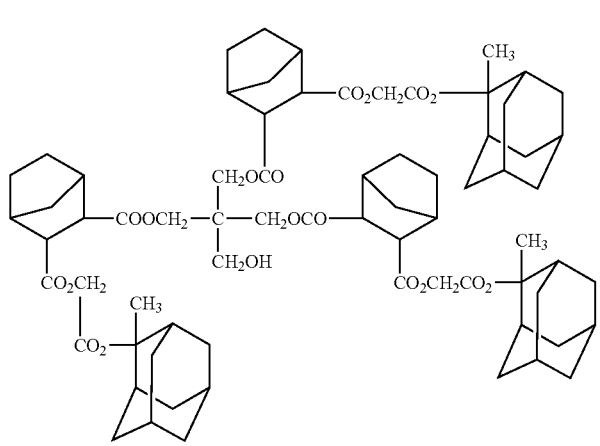

PENB-3AMAD

The experiment was conducted in the same manner as in Example 8 except that the amount of NBEAD and of CAMAD were changed to obtain triester compound (abbreviated to "PENB-3 AMAD") via tricarboxylic acid (abbreviated to "PENB-3 A"). (melting point: 96-98° C.)

LC-MS: (PENB-3A) 673.1(M+K)$^+$ ($C_{32}H_{42}O_{13}$=634.67) LC-MS: (PENB-3AMAD)1291.5 (M+K)$^+$ ($C_{71}H_{96}O_{19}$=1253.51) $^1$H NMR (CDCl$_3$):d1.45-2.10 (54H, adamantyl and norbornyl), 1.62 (9H, CH$_3$), 2.28 (6H, m, adamantyl), 2.54-2.63 (6H, norbornyl), 2.78 (1H, OH), 2.96-3.13 (6H, norbornyl), 3.47 (2H, m, methylene), 3.93-4.12 (6H, m, methylene), 4.34-4.73 (6H, m, methylene) $^{13}$C NMR (CDCl$_3$):d22.25 (CH$_3$), 23.69 and 24.06 (norbornyl), 26.49 (adamantyl), 27.19 (adamantyl), 32.87 (adamantyl), 34.42 (adamantyl), 36.12 and 36.22 (adamantyl), 37.99 (adamantyl), 39.76 (norbornyl), 40.11 (norbornyl), 40.23 (norbornyl), 40.36 and 40.39 and 40.44 and 40.48 (norbornyl), 43.30 (quaternary carbon), 46.31 and 46.72 (norbornyl), 60.27 (CH$_2$), 60.83 (CH$_2$), 62.11 (CH$_2$), 88.97 (adamantyl), 166.56 and 166.59 and 166.61 (C=O), 171.82 and 171.83 and 171.87 (C=O), 172.18 and 172.23 (C=O)

EXAMPLE 10

Synthesis of PENB-2AMAD-2AHAD

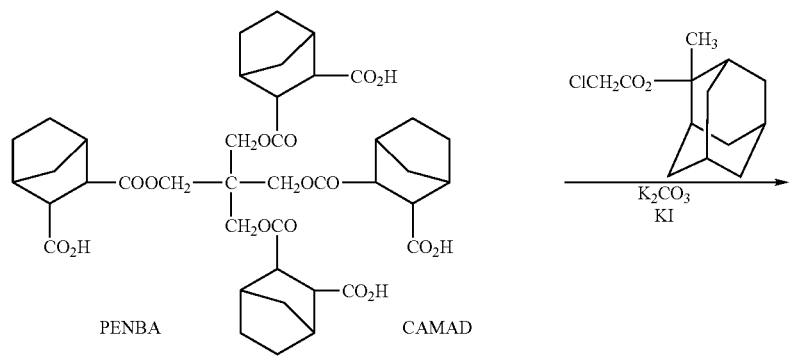

PENBA     CAMAD

-continued

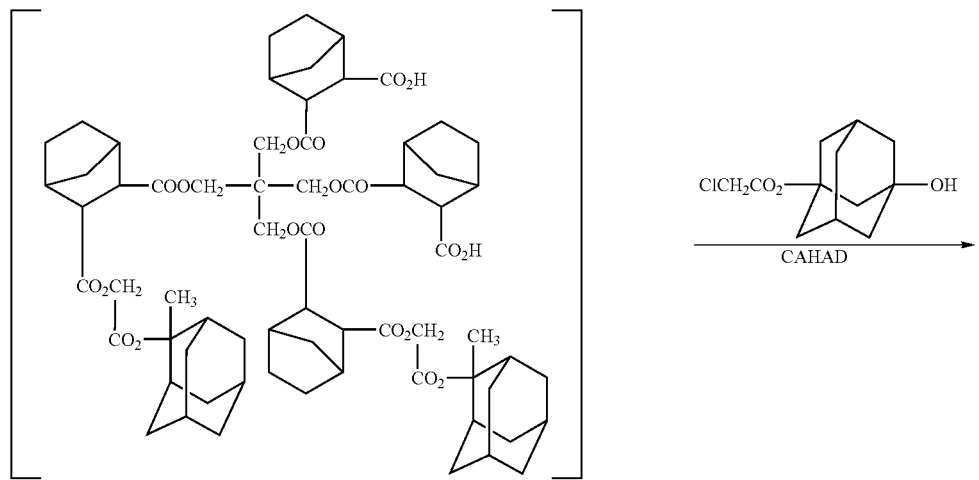

CAHAD

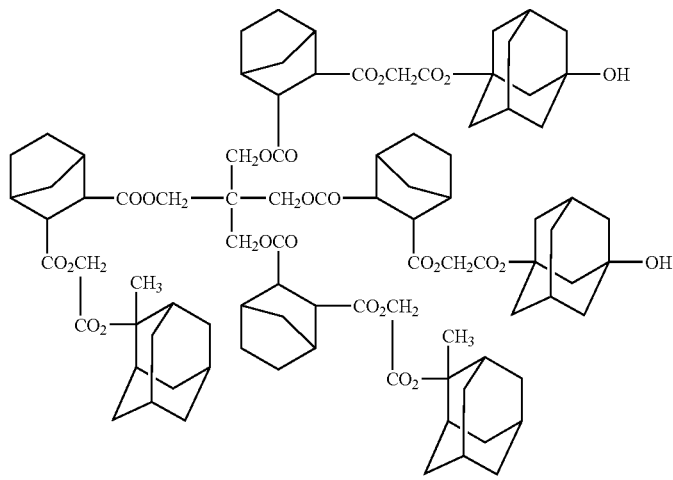

PENB-2AMD-2AHD 40.0 g of PENBA was dissolved in 392 g of DMF. 25.5 of CAMAD, 41.4 g of potassium carbonate and 0.83 g of potassium carbonate were added thereto, and the mixture was stirred at 40° C. for 5.5 hours. The mixture was further stirred at room temperature overnight. To the reaction mixture, 25.7 g of CAHAD was added, and the added mixture was stirred at 40° C. for 5.5 hours. The mixture was further stirred at room temperature overnight. The resulting mixture was diluted with water, and then was extracted with ethyl acetate. The organic layer was washed with water, dried with anhydrous magnesium sulfate, and then concentrated. The concentrate was purified by silica gel column chromatography to obtain 5.5 g of tetraester2/2 compound (abbreviated to "PENB-2AMAD-2AHAD")

GPC-MS: (PENB-2-AMAD-2AHAD) 1670.9(M+K)$^+$ ($C_{90}H_{118}O_{27}$=1631.88).

EXAMPLE 11
Synthesis of PENB-2AMAD-AHAD
The experiment was conducted in the same manner as in Example 10 except that the amount of CAMAD and of CAHAD were changed to obtain triester2/1 compound (abbreviated to "PENB-2AMAD-AHAD").
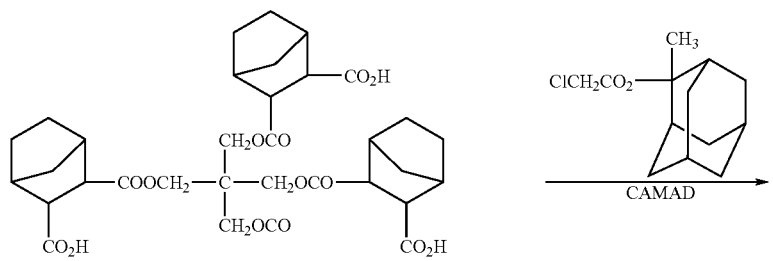
PENB-3A
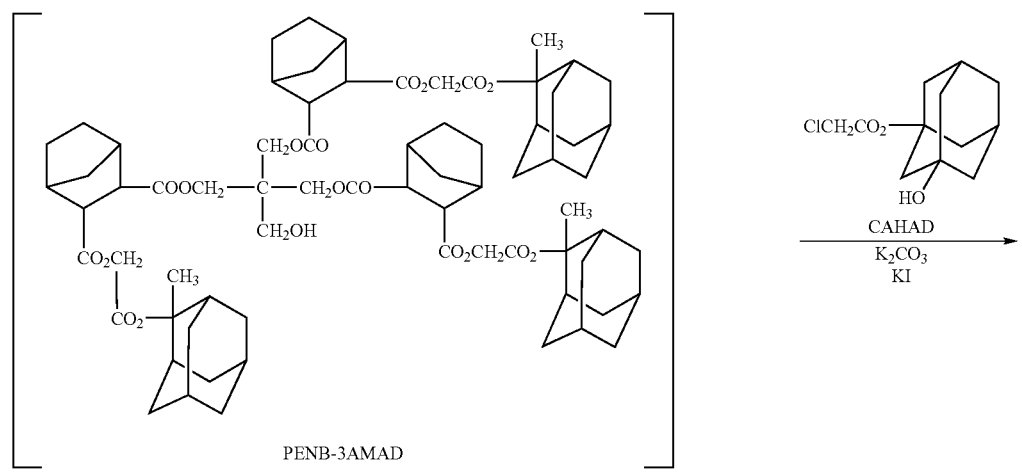
PENB-3AMAD
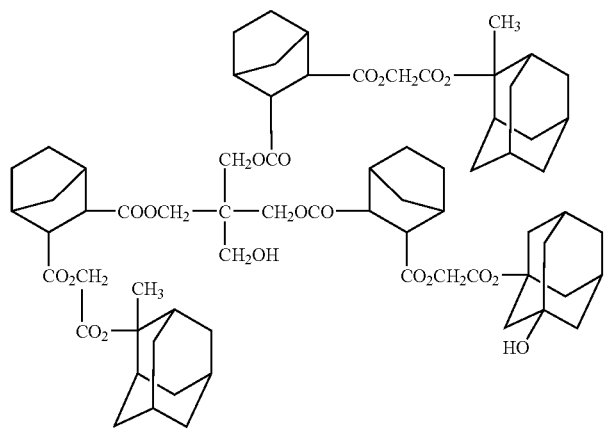
PENB-2AMAD-AHD

GPC-MS: (PENB-2-AMAD-AHAD) 1294(M+K)$^+$ (C$_{70}$H$_{94}$O$_{20}$=1255.48)

EXAMPLE 12

Synthesis of PECH-CHX

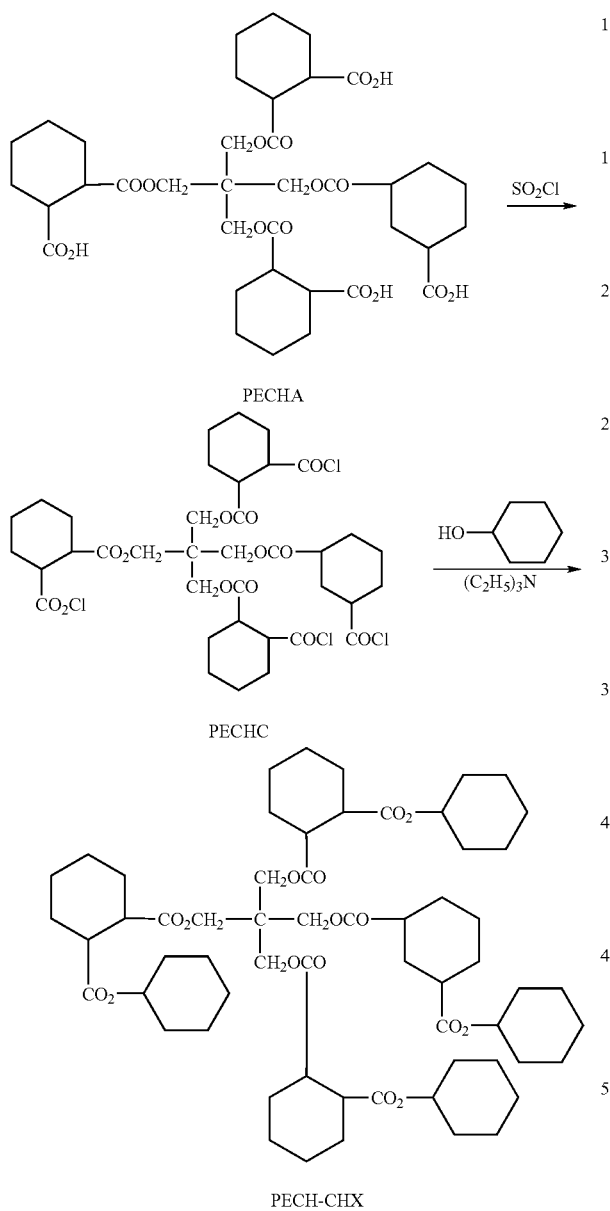

PECHA

PECHC

PECH-CHX 2.0 g of PECHA and 1.9 g of thionyl chloride were mixed in 50 ml of toluene. The mixture was refluxed for 0.5 hour. The resulting mixture was concentrated under reduced pressure to obtain carboxylic acid halide (abbreviated to "PECHC").

$^1$H NMR (CDCl$_3$):d1.47-1.50 (16H, cyclohexyl), 1.82-2.11 (16H, cyclohexyl), 3.01 (4H, cyclohexyl), 3.19 (4H, cyclohexyl), 4.07-4.18 (8H, methylene) $^{13}$C NMR (CDCl$_3$):d23.11&23.42 (cyclohexyl), 25.98 (cyclohexyl), 26.61 (cyclohexyl), 42.19 (quaternary carbon), 43.42 (cyclohexyl), 53.98 (cyclohexyl), 61.92 (methylene), 171.83 (C=O from ester), 175.02 (C=O from acid halide) GPC-MS: (PECHC) 863(M+K)$^+$ (C$_{37}$H$_{48}$Cl$_4$O$_{12}$=826.58)

To a solution consisting of 1.6 g of cyclohexanol, 1.6 g of triethylamine and 20 ml of THF, a solution consisting of 2.9 g of PECHC and 20 ml of THF was added dropwise. After stirred for three days, the reaction mixture was diluted with water, and then extracted with ethyl acetate. The organic layer obtained was washed with water, dried with anhydrous magnesium sulfate, and then concentrated. 3.2 g of the crude product obtained was purified by silica gel column chromatography (developer: hexane/ethyl acetate) to obtain 1.5 g of tetraester (abbreviated to "PECH—CHX").

GPC-MS: (PECH—CHX) 1120(M+K)$^+$ (C$_{61}$H$_{92}$O$_{16}$=1081.37)

EXAMPLE 13

Synthesis of PENBOM

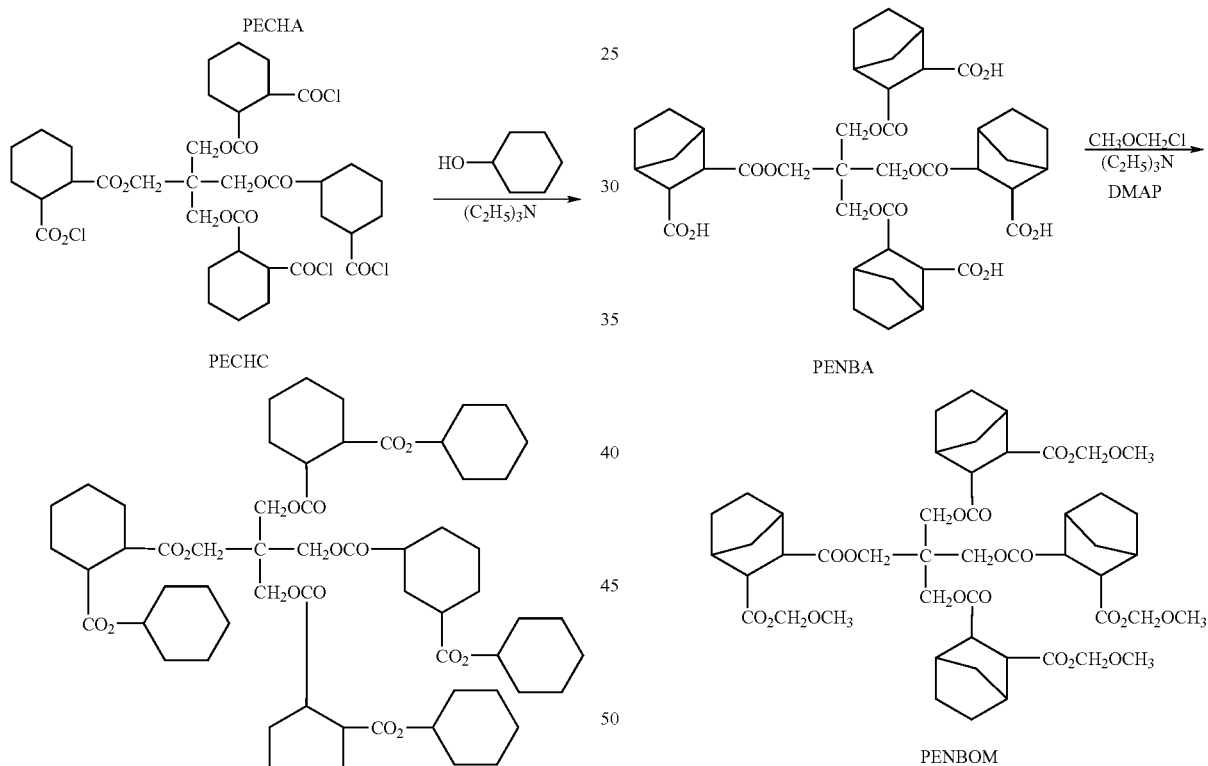

PENBA

PENBOM

To a solution obtained by dissolving 30 g of PENBA and 15.1 g of chloromethyl methyl ether in 150 ml of DMF, a solution consisting of 30.3 g of TEA, 1.2 g of DMAP and 50 ml of DMF was added dropwise at 3 to 8° C. for 3 hours. After stirred at room temperature overnight, the reaction mixture was diluted with water, and then extracted with ethyl acetate. The organic layer obtained was washed with water, with sodium bicarbonate solution, and with Water. The washed layer was dried with anhydrous magnesium sulfate, and then concentrated to obtain 40 g or crude product. The crude product was purified by silica gel chromatography to obtain 20.4 g of tetracarboxylic ester (abbreviated to "PENBOM").

GPC-MS:999 (M+Na)$^+$ (C$_{49}$H$_{68}$O$_{20}$=977.05)

EXAMPLE 14
Synthesis of PECHECHNL
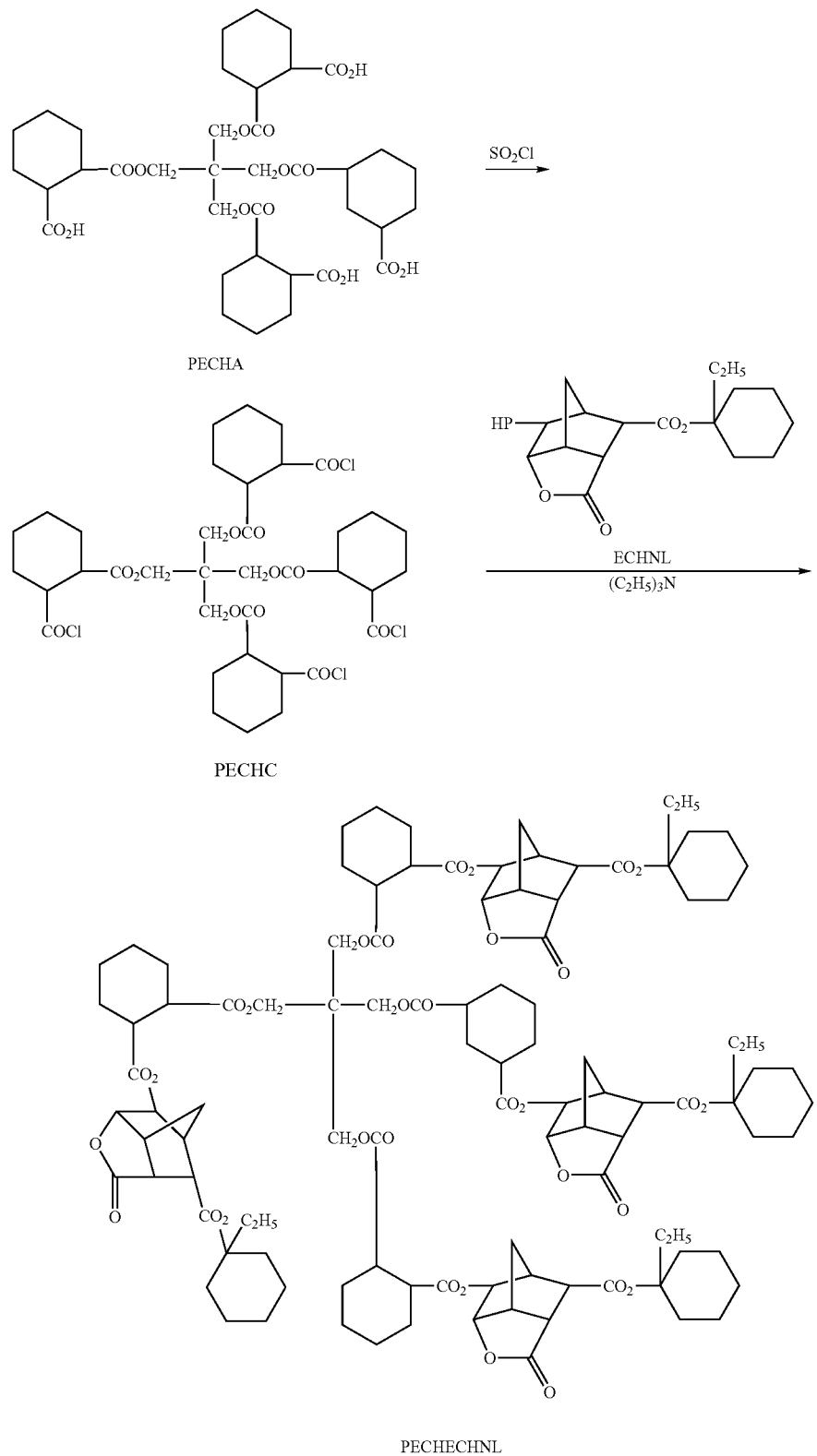

PECHC was synthesized in the same manner as in Example 12. To a solution consisting of 3.6 g of 2-hydroxy-7-(1-ethylcyclohexyloxy)carbonyl-4-oxytricyclo[4.2.1.03.7]nonan-5-one (abbreviated to "ECHNL", described in JP2005-8531-A), 1.6 g of triethylamine and 20 ml of THF, a solution consisting of 2.2 g of PECHC and 20 ml of THF was added dropwise. After stirred for two days, the reaction mixture was diluted with water, and then extracted with ethyl acetate. The organic layer obtained was washed with water, dried with anhydrous magnesium sulfate, and then concentrated. 6.7 g of the crude product obtained was purified by silica gel column chromatography (developer: hexane/ethyl acetate) to obtain 4.6 g of tetraester (abbreviated to "PECHECHNL").

GPC-MS: (PECHECHNL) 1913(m/z)$^+$ ($C_{105}H_{140}O_{32}$=1914.22)

Polymer Synthesis Example 1

2-ethyl-2-adamantyl methacrylate, 3-hydroxy-1-adamantyl methacrylate and 5-methacryloyloxy-2,6-norbornanlactone were charged in a vessel in molar ratio of 2:1:1 (11.2 g:5.3 g:5.0 g), and then 50 g of 1,4-dioxane was added thereto to obtain a solution. To the solution, azobisisobutyronitrile was added in an amount of 2% by mol to total amount of monomers. The added solution was heated and stirred at 85° C. for 5 hours. The reaction mixture was poured into a large quantity of heptane to crystallize. The crystallization was further repeated twice to obtain 6.3 g of polymer having weight average molecular weight of 9300. The polymer is called as Polymer A.

EXAMPLES 15 TO 29 AND COMPARATIVE EXAMPLES 1 TO 2

The following components were mixed and dissolved, further, filtrated through a fluorine resin filter having pore diameter of 0.2 µm, to prepare resist liquid.

<Polymer>
10 parts of Polymer A synthesized according to Polymer Synthesis Example 1 above described in Table 1.

<Acid Generator>
Si: 0.2 part of (4-methylphenyl)diphenylsulfonium perfluorobutanesulfonate <Quencher>
Q: 0.0075 part of 2,6-diisopropylaniline <Solvent>
Y: 51.5 parts of propylene glycol monomethyl ether acetate, 35.0 parts of 2-heptanone and 3.5 parts of γ-butyrolactone <Supracompound>
0.25 part of Supracompound described in Table 1

Silicon wafers were each coated with "ARC-29A8", which is an organic anti-reflective coating composition available from Brewer Co., and then baked under the conditions: 215° C., 60 seconds, to form a 780 Å-thick organic anti-reflective coating. Each of the resist liquids prepared as above was spin-coated over the anti-reflective coating so that the thickness of the resulting film became 0.25 µm after drying. The silicon wafers thus coated with the respective resist liquids were each prebaked on a direct hotplate at 130° C. for 60 seconds. Using an ArF excimer stepper ("NSR ArF" manufactured by Nikon Corporation, NA=0.55, 2/3 Annular), each wafer thus formed with the respective resist film was subjected to line and space pattern exposure, with the exposure quantity being varied stepwise.

After the exposure, each wafer was subjected to post-exposure baking on a hotplate at temperature shown in "PEB" column in Table 1 for 60 seconds and then to puddle development for 60 seconds with an aqueous solution of 2.38 wt % tetramethylammonium hydroxide.

Each of a dark field pattern developed on the organic anti-reflective coating substrate after the development was observed with a scanning electron microscope, the results of which are shown in Table 1. The term "dark field pattern", as used herein, means a pattern obtained by exposure and development through a reticle comprising chromium base surface (light-shielding portion) and linear glass layers (light-transmitting portion) formed in the chromium surface and aligned with each other. Thus, the dark field pattern is such that, after exposure and development, resist layer surrounding the line and space pattern remains on substrate.

Effective Sensitivity:
It is expressed as the amount of exposure that the line pattern (light-shielding layer) and the space pattern (light-transmitting layer) become 1:1 after exposure through 0.13 µm line and space pattern mask and development.

Resolution:
It is expressed as the minimum size of space pattern which gave the space pattern split by the line pattern at the exposure amount of the effective sensitivity.

Line Edge Roughness
When line edge roughness is very good, its evaluation is marked by "○".
When line edge roughness is good, its evaluation is marked by "Δ".
When line edge roughness is poor, its evaluation is marked by "X".

TABLE 1

| Example No. | Supracompound | PEB (° C.) | Effective Sensitivity | Resolution | Line Edge Roughness |
|---|---|---|---|---|---|
| Example 15 | PECHOM | 120 | 30.5 | 0.13 | ○ |
| Example 16 | PECH-AMAD | 125 | 23 | 0.12 | ○ |
| Example 17 | PECH-AHAD | 125 | 26 | 0.12 | ○ |
| Example 18 | PECH-ANL | 125 | 23 | 0.12 | ○ |
| Example 19 | PECH-3-AMAD-ANL | 125 | 26 | 0.12 | Δ |
| Example 20 | PECH-2-AMAD-2-ANL | 125 | 23 | 0.12 | ○ |
| Example 21 | GLUCH-5AMAD | 125 | 21.5 | 0.12 | ○ |
| Example 22 | GLUCH-4AMAD | 125 | 24.5 | 0.12 | ○ |
| Example 23 | PENB-4AMAD | 125 | 26 | 0.12 | ○ |
| Example 24 | PENB-3AMAD | 125 | 24.5 | 0.12 | ○ |
| Example 25 | PENB-2-AMAD-2AHAD | 125 | 29 | 0.12 | ○ |
| Example 26 | PENB-2-AMAD-AHAD | 125 | 23 | 0.12 | ○ |
| Example 27 | PECH-CHX | 120 | 25 | 0.12 | ○ |
| Example 28 | PENBOM | 120 | 30 | 0.13 | ○ |
| Example 29 | PECHECHNL | 125 | 24 | 0.12 | ○ |
| Comparative Example 1 | none | 120 | 32 | 0.13 | X |
| Comparative Example 2 | none | 125 | 24.5 | 0.12 | X |

As is apparent from Table 1, the resists of the Examples 15 to 29 that represent the present composition showed results that line edge roughness was excellent while presenting equal or higher sensitivity and resolution compared to the resists of Comparative Examples 1 and 2.

The chemically amplified positive resist composition of the present invention that contains polymer, an acid generator and Supracompound is excellent in various resist perfor-

What is claimed is:

1. A chemically amplified positive resist composition comprising
(i) a polymer which is insoluble or poorly soluble in an alkali aqueous solution but becomes soluble in an alkali aqueous solution by the action of an acid,
(ii) an acid generator, and
(iii) a compound of the formula (I)

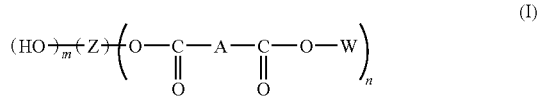
(I)

wherein Z represents hydrocarbon group having 2 to 14 carbon atom, and at least one of —$CH_2$— except the one bonding to other group adjacent to Z may be substituted by —O—; A represents divalent alicyclic hydrocarbon group having 3 to 14 carbon atoms; W represents hydrogen atom, alkyl group having 1 to 12 carbon atoms, alkoxyalkyl group having 2 to 12 carbon atoms, or a group of the formula (II)

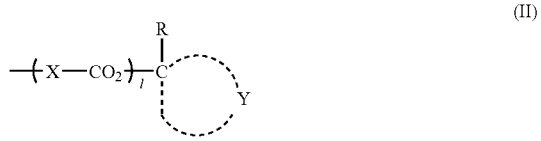
(II)

wherein X represents divalent connecting group, R represents hydrogen atom, alkyl group having 1 to 6 carbon atoms or cycloalkyl group having 3 to 6 carbon atoms, Y represents atoms necessary to form an alicyclic hydrocarbon group together with the adjacent carbon atom and contains 4 to 12 carbon atoms, and at least one of —$CH_2$— in the alicyclic hydrocarbon group may be substituted by —CO— or —O—, and at least one of hydrogen atoms in the alicyclic hydrocarbon group may be substituted by alkyl group having 1 to 4 carbon atoms, alkoxy group having 1 to 4 carbon atoms, trifluoromethyl group, hydroxyl group or cyano group, and 1 represents 0 or 1, and each of m and n shows an integer satisfying the following inequalities:

$0 \leq m \leq 13$, $1 \leq n \leq 14$, $2 \leq m+n \leq 14$, and when n is 2 or more, each of A is the same or different, and also each of W is the same or different.

2. The composition according to claim 1, wherein Z is saturated acyclic hydrocarbon group having 2 to 14 carbon atoms or saturated alicyclic hydrocarbon group having 3 to 14 carbon atoms, wherein at least one of —$CH_2$— group except the one bonding to other group adjacent to Z may be substituted by —O—; A is divalent saturated alicyclic hydrocarbon group; and X is divalent saturated acyclic hydrocarbon group or divalent saturated alicyclic hydrocarbon group, wherein at least one of —$CH_2$— in the hydrocarbon group except the one bonding to other group adjacent to X may be substituted by —O—, —COO— or —O—CO—.

3. The composition according to claim 1, wherein the compound of the formula (I) is a compound of the formula (III)

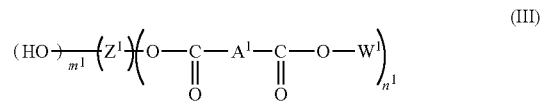
(III)

wherein $Z^1$ represents a hydrocarbon group having 3 to 6 carbon atoms, and at least one of —$CH_2$— except the one bonding to other group adjacent to $Z^1$ may be substituted by —O—; $A^1$ represents divalent alicyclic hydrocarbon group having 5 to 10 carbon atoms; $W^1$ represents hydrogen atom, alkyl group having 1 to 10 carbon atoms, alkoxyalkyl group having 2 to 6 carbon atoms, or a group of the formula (IV)

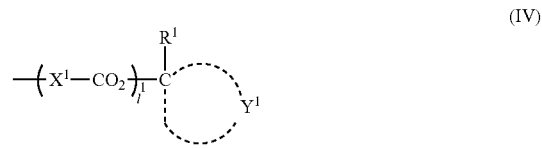
(IV)

wherein $X^1$ represents methylene group, ethylene group, trimethylene group, tetramethylene group, or 6-hydroxy-2-norbornanecarboxylic acid γ-lactone-3,5-diyl group, $R^1$ represents hydrogen atom, alkyl group having 1 to 4 carbon atoms or cycloalkyl group having 3 to 6 carbon atoms, $Y^1$ represents atoms necessary to form an alicyclic hydrocarbon group together with the adjacent carbon atom and contains 4 to 10 carbon atoms, and at least one of —$CH_2$— in the alicyclic hydrocarbon group may be substituted by —CO— or —O—, and at least one of hydrogen atoms in the alicyclic hydrocarbon group may be substituted by alkyl group having 1 to 6 carbon atoms, alkoxy group having 1 to 6 carbon atoms, perfluoroalkyl group having 1 to 4 carbon atoms, hydroxyl group or cyano group, and $1^1$ represents 0 or 1, and $m^1$ and $n^1$ shows an integer satisfying all of the following inequalities:

$0 \leq m^1 \leq 13$, $1 \leq n^1 \leq 14$, $2 \leq m^1+n^1 \leq 14$, and when $n^1$ is 2 or more, each of $A^1$ is the same or different, and each of $W^1$ is the same or different.

4. The composition according to claim 3, wherein $Z^1$ is saturated acyclic hydrocarbon group having 3 to 6 carbon atoms or saturated alicyclic hydrocarbon group having 3 to 6 carbon atoms, wherein at least one of —$CH_2$— group except the one bonding to other group adjacent to $Z^1$ may be substituted by —O—; and $A^1$ is divalent saturated alicyclic hydrocarbon group having 5 to 10 carbon atoms.

5. The composition according to claim 1, wherein the compound of the formula (I) is a compound of the formula (V)

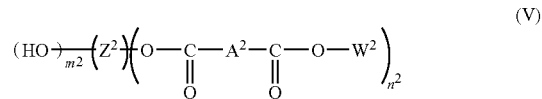
(V)

wherein $Z^2$ represents a group selected by the following formulae

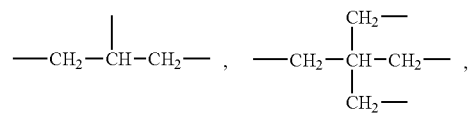

-continued

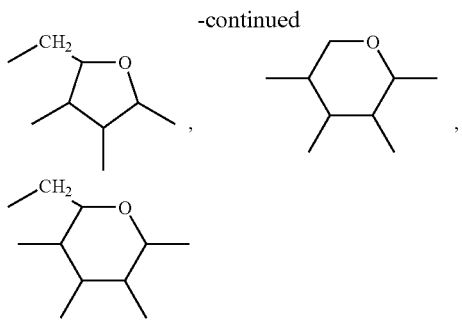

wherein a straight line with an open end shows a bond which is extended from an adjacent carbon atom and which does not specify a group to be bonded, $A^2$ represents cyclopentylene group, cyclohexylene group, norbornylene group or adamantylene group; $W^2$ represents hydrogen atom, methyl group, ethyl group, isopropyl group, butyl group, methoxymethyl group, ethoxymethyl group, propoxymethyl group, methoxyethyl group, ethoxyethyl group, or a group of the formula (VI)

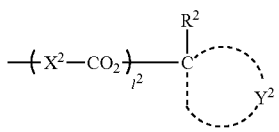 (VI)

wherein $X^2$ represents methylene group or ethylene group, $R^2$ represents hydrogen atom, methyl group, ethyl group, isopropyl group, butyl group, cyclopentyl group or cyclohexyl group, $Y^2$ represents atoms necessary to form cyclopentyl group, cyclohexyl group, norbornyl group or adamantyl group together with the adjacent carbon atom, and at least one of —$CH_2$— in the cyclopentyl group, cyclohexyl group, norbornyl group or adamantyl group may be substituted by —CO— or —O—, and at least one of hydrogen atoms in the cyclopentyl group, cyclohexyl group, norbornyl group or adamantyl group may be substituted by methyl group, ethyl group, isopropyl group, butyl group, methoxy group, ethoxy group, propoxy group, trifluoromethyl group, hydroxyl group or cyano group, and $l^2$ represents 0 or 1, and $m^2$ and $n^2$ shows an integer satisfying all of the following inequalities:

$0 \leq m^2 \leq 4$, $1 \leq n^2 \leq 5$, $2 \leq m^2 + n^2 \leq 5$, and when $n^2$ is 2 or more, each of $A^2$ is the same or different, and also each of $W^2$ is the same or different.

6. An ester derivative of the formula (VII)

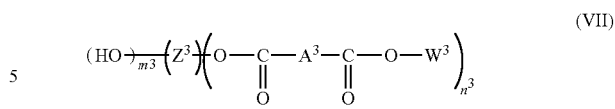 (VII)

wherein $Z^3$ represents hydrocarbon group having 2 to 14 carbon atom, and at least one of —$CH_2$— except the one bonding to other group adjacent to $Z^3$ may be substituted by —O—; $A^3$ represents divalent alicyclic hydrocarbon group having 3 to 14 carbon atoms; $W^3$ represents hydrogen atom, alkyl group having 1 to 12 carbon atoms or a group of the formula (VIII)

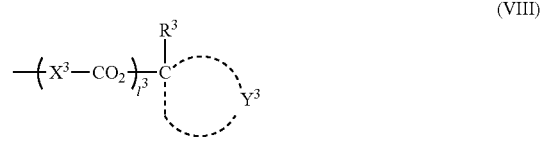 (VIII)

wherein $X^3$ represents divalent connecting group, $R^3$ represents hydrogen atom, alkyl group having 1 to 6 carbon atoms or cycloalkyl group having 3 to 6 carbon atoms, $Y^3$ represents atoms necessary to form an alicyclic hydrocarbon group together with the adjacent carbon atom and contains 3 to 12 carbon atoms, and at least one of —$CH_2$— in the alicyclic hydrocarbon group may be substituted by —CO— or —O—, and at least one of hydrogen atoms in the alicyclic hydrocarbon group may be substituted by alkyl group having 1 to 6 carbon atoms, alkoxy group having 1 to 6 carbon atoms, perfluoroalkyl group having 1 to 4 carbon atoms, hydroxyl group or cyano group, and $l^3$ represents 0 or 1, and $m^3$ and $n^3$ show an integer satisfying all of the following inequalities, $0 \leq m^3 \leq 13$ $1 \leq n^3 \leq 14$, $2 \leq m^3 + n^3 \leq 14$, and when $n^3$ is 2 or more, each of $A^3$ is the same or different, and also each of $W^3$ is the same or different.

7. The ester derivative according to claim 6, wherein $Z^3$ is saturated acyclic hydrocarbon group having 2 to 14 carbon atoms or saturated alicyclic hydrocarbon group having 3 to 14 carbon atoms, wherein at least one of —$CH_2$— group except the one bonding to other group adjacent to $Z^3$ may be substituted by —O—; $A^3$ is divalent saturated alicyclic hydrocarbon group; and $X^3$ is divalent saturated acyclic hydrocarbon group or divalent saturated alicyclic hydrocarbon group, wherein at least one of —$CH_2$— in the hydrocarbon group except the one bonding to other group adjacent to $X^3$ may be substituted by —O—, —COO— or —O—CO—.

* * * * *

UNITED STATES PATENT AND TRADEMARK OFFICE
CERTIFICATE OF CORRECTION

PATENT NO. : 7,625,689 B2  Page 1 of 1
APPLICATION NO. : 11/303925
DATED : December 1, 2009
INVENTOR(S) : Takemoto et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 395 days.

Signed and Sealed this

Second Day of November, 2010

David J. Kappos
*Director of the United States Patent and Trademark Office*